(12) United States Patent
Chen et al.

(10) Patent No.: US 8,257,932 B2
(45) Date of Patent: Sep. 4, 2012

(54) INTERFACING NANOSTRUCTURES TO BIOLOGICAL CELLS

(75) Inventors: Xing Chen, Allston, MA (US); Carolyn R. Bertozzi, Berkeley, CA (US); Alexander K. Zettl, Albany, CA (US)

(73) Assignee: The Regents of the University of California, Oakland, CA (US)

( * ) Notice: Subject to any disclaimer, the term of this patent is extended or adjusted under 35 U.S.C. 154(b) by 1058 days.

(21) Appl. No.: 12/034,388

(22) Filed: Feb. 20, 2008

(65) Prior Publication Data
US 2008/0199399 A1    Aug. 21, 2008

Related U.S. Application Data

(60) Provisional application No. 60/902,408, filed on Feb. 21, 2007.

(51) Int. Cl.
*G01N 33/53* (2006.01)
(52) U.S. Cl. .................... 435/7.1; 435/7.21; 424/9.1
(58) Field of Classification Search .................. None
See application file for complete search history.

(56) References Cited

U.S. PATENT DOCUMENTS

| | | | |
|---|---|---|---|
| 5,144,011 A | 9/1992 | Shen et al. | |
| 5,641,466 A | 6/1997 | Ebbesen et al. | |
| 5,997,832 A | 12/1999 | Lieber et al. | |
| 6,036,774 A | 3/2000 | Lieber et al. | |
| 6,063,629 A | 5/2000 | Knoblauch et al. | |
| 6,812,206 B2 | 11/2004 | Wands et al. | |
| 6,821,730 B2 | 11/2004 | Hannah | |
| 2003/0134333 A1 | 7/2003 | Dehlinger et al. | |
| 2004/0023855 A1* | 2/2004 | John et al. | 514/8 |
| 2005/0191427 A1 | 9/2005 | Wade et al. | |
| 2006/0275371 A1 | 12/2006 | Dai et al. | |

FOREIGN PATENT DOCUMENTS
WO    WO 2008133755 A1    11/2008

OTHER PUBLICATIONS

Liu Z. et al. In vivo biodistribution and highly efficient tumour targeting of carbon nanotubes in mice, Nature Nanotechnology, Jan. 2007, vol. 2, pp. 52 (supplemetary material included), published online Dec. 17, 2006.*
Schirrmann T. et al. Tumor-specific targeting of a cell line with natural killer activity by asialoglycoprotein receptor gene transfer, Cancer Immunol. Immunother., 2001, vol. 50, pp. 549-556.*
Monteiro-Riviere et al., Multi-walled carbon nanotube interactions with human epidermal keratinocytes, Toxicology Letters, 2005, vol. 155, pp. 377-384.*
Winter J. O. (2006) Nanoparticles and Nanowires for Cellular Engineering, Chapter 11, pp. 388-460, Nanotechnologies for the Life Sciences vol. 9, Tissue, Cell and Organ Engineering. Edited by Challa S. S. R. Kumar, Wiley-VCH Verlag GmbH & Co. KGaA, Weinheim.*
Russell-Jones G.J. et al. Lectin-mediated transport of nanoparticles across Cacao-2 and OK cells, International Journal of Pharmaceutics, 1999, vol. 190, pp. 165-174.*
Polysciences Inc., Technical data sheet 431, Aug. 2009, Fluoresbrite® Microparticles, pp. 1-3.*
Menezes C.A. et al. Inhibition of *Escherichia coli* heat-labile enterotoxin by neoglycoprotein and anti-lectin antibodies which mimic GM1 receptor, FEMS Microbiology Letters, 2002. vol. 216, pp. 67-70.*
Umamaheshwari R.B. et al. Receptor Mediated Targeting of Lectin Conjugated Gliadin Nanoparticles in the Treatment of *Helicobacter pylori*, Journal of Drug Targeting, Aug. 2003, vol. 11, No. 7, pp. 415-424.*
Xing Chen, et al., "Interfacing Carbon Nanotubes with Living Cells," J. Am. Chem. Soc., 2006, vol. 128, 6292-6293.
Xing Chen, et al., "Biomimetic Engineering of Carbon Nanotubes by Using Cell Surface Mucin Mimics," Agnew. Chem. Int. Ed., 2004, vol. 43, 6112-6116.
George A. Orr, et al., "Synthetic concanavalin a receptors and erythrocte agglutination," Nature, Apr. 2, 1978, vol. 272, 722-725.
Ola Blixt, et al., "Printed covalent glycan array for ligand profiling of diverse glycan binding proteins," PNAS, Dec. 7, 2004, vol. 101, No. 49, 17033-17038.
Hiroyuki Keshi, et al., "Identification and Characterization of a Novel Human Collectin CL-K1," Microbiol. Immunol., 2006, vol. 50, No. 12, 1001-1013.
Catherine Robbe, et al., "Structural diversity and specific distribution of O-glycans in normal human mucins along the intestinal tract," Biochem J., 2004, vol. 384, 307-316.
Alex Perry, et al., "Inhibition of Blood Clearance and Hepatic Tissue Binding of *Escherichia coli* by Liver Lectin-Specific Sugars and Glycoproteins," Infection and Immunity, Jan. 1984, 257-262.
K. C. Kim, et al., "Airway goblet cell mucin: its structure and regulation of secretion," Eur. Resp. J., 1997, vol. 10, 2644-2649.
Anna Zalewska, et al., "Structure and biosynthesis of human salivary mucins," Acta Biochimica Polonica, 2000, vol. 47, No. 4, 1067-1079.
Cai et al., "Highly efficient molecular delivery into mammalian cells using carbon nanotube spearing," Nat. Methods 2:449-454 (Jun. 2005).
Martinez et al., "Length control and sharpening of atomic force microscope carbon nanotube tips assisted by an electron beam," Nanotechnology 16:2493-2496 (Sep. 13, 2005).

* cited by examiner

*Primary Examiner* — Jon P Weber
*Assistant Examiner* — Satyendra Singh
(74) *Attorney, Agent, or Firm* — David J. Aston; Peters Verny, LLP

(57) ABSTRACT

Disclosed herein are methods and materials by which nanostructures such as carbon nanotubes, nanorods, etc. are bound to lectins and/or polysaccharides and prepared for administration to cells. Also disclosed are complexes comprising glycosylated nanostructures, which bind selectively to cells expressing glycosylated surface molecules recognized by the lectin. Exemplified is a complex comprising a carbon nanotube functionalized with a lipid-like alkane, linked to a polymer bearing repeated α-N-acetylgalactosamine sugar groups. This complex is shown to selectively adhere to the surface of living cells, without toxicity. In the exemplified embodiment, adherence is mediated by a multivalent lectin, which binds both to the cells and the α-N-acetylgalactosamine groups on the nanostructure.

19 Claims, 9 Drawing Sheets

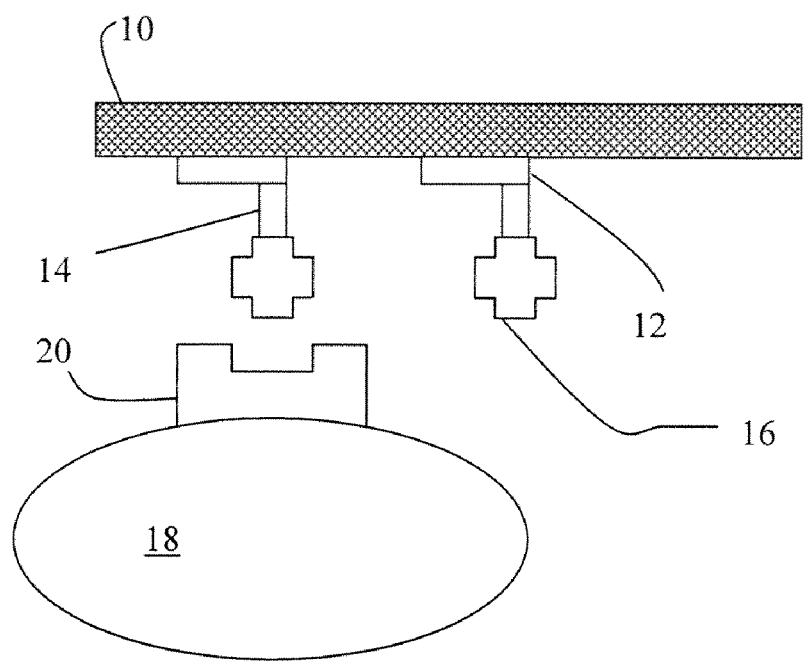
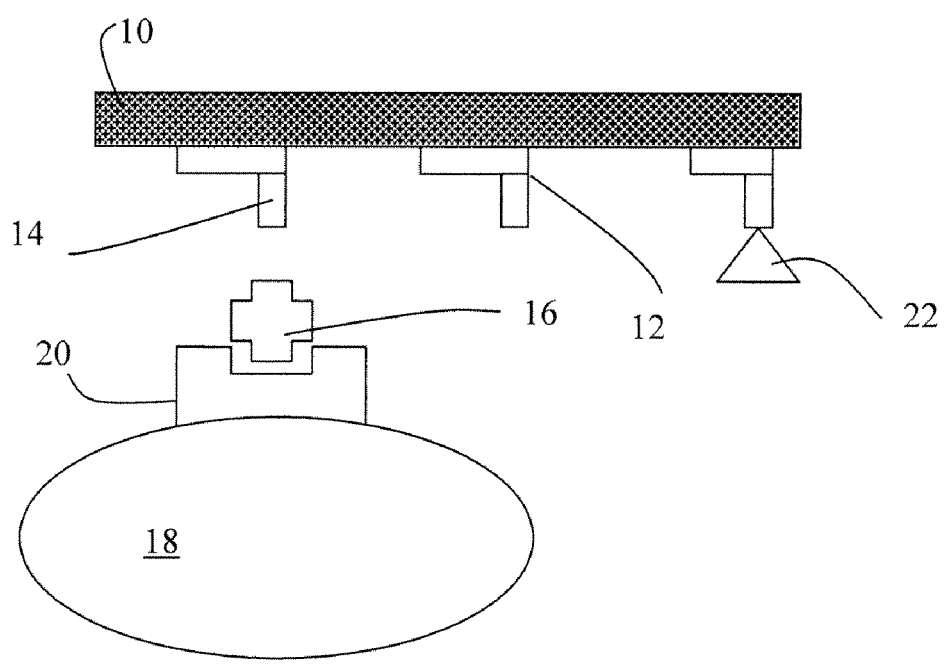
Fig. 1A-B

3A
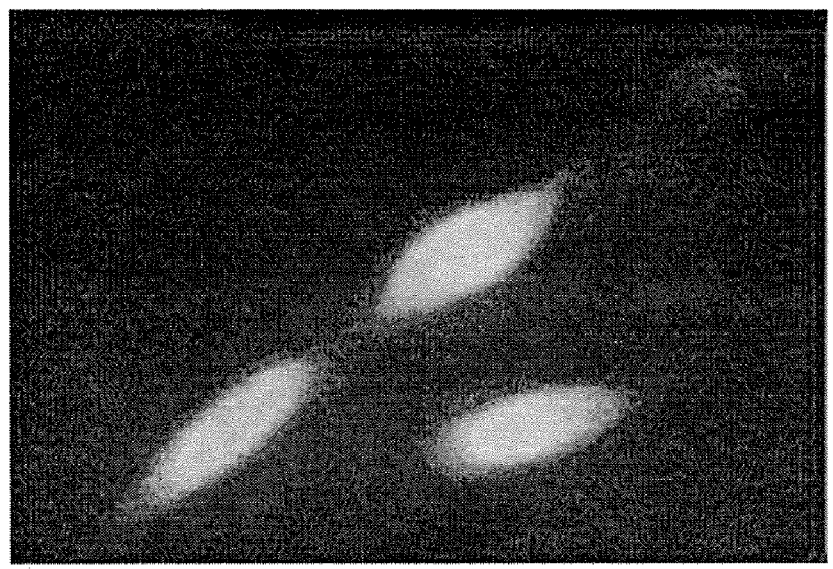
3B
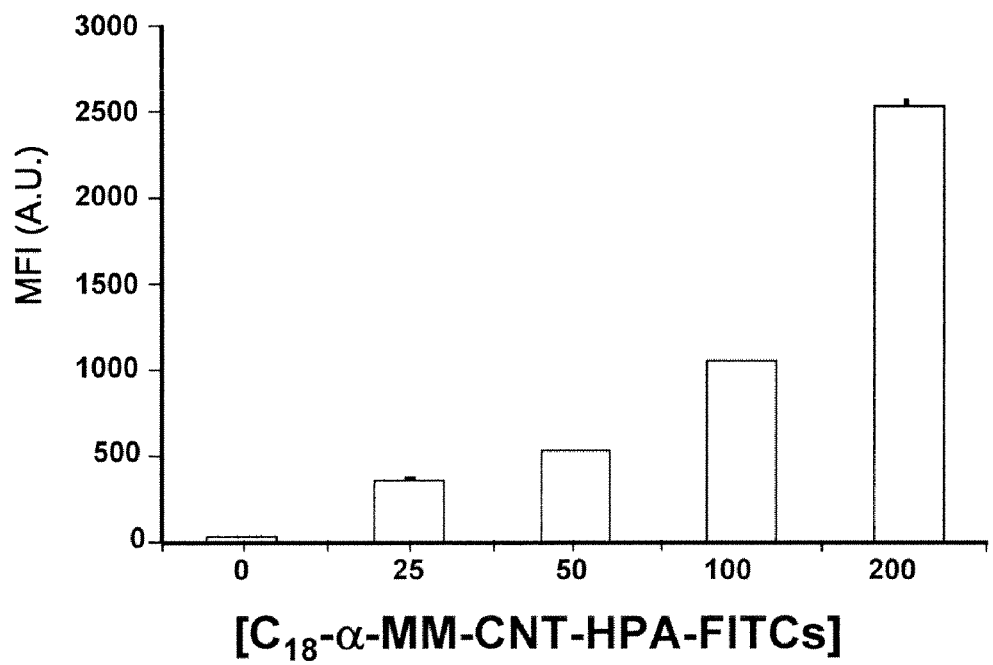
Fig. 3A-B

4A
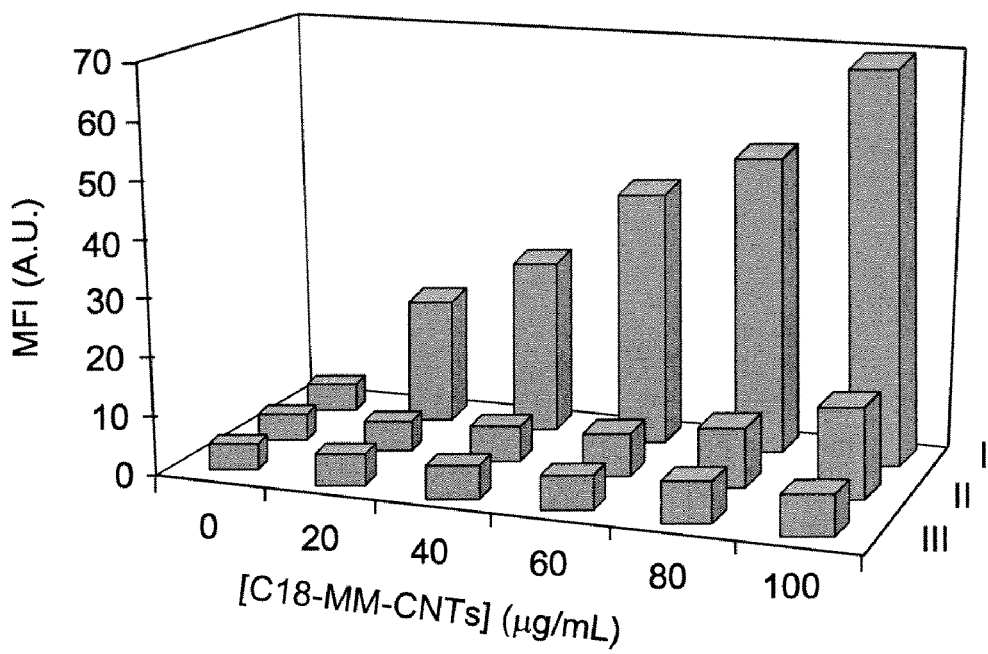
4B
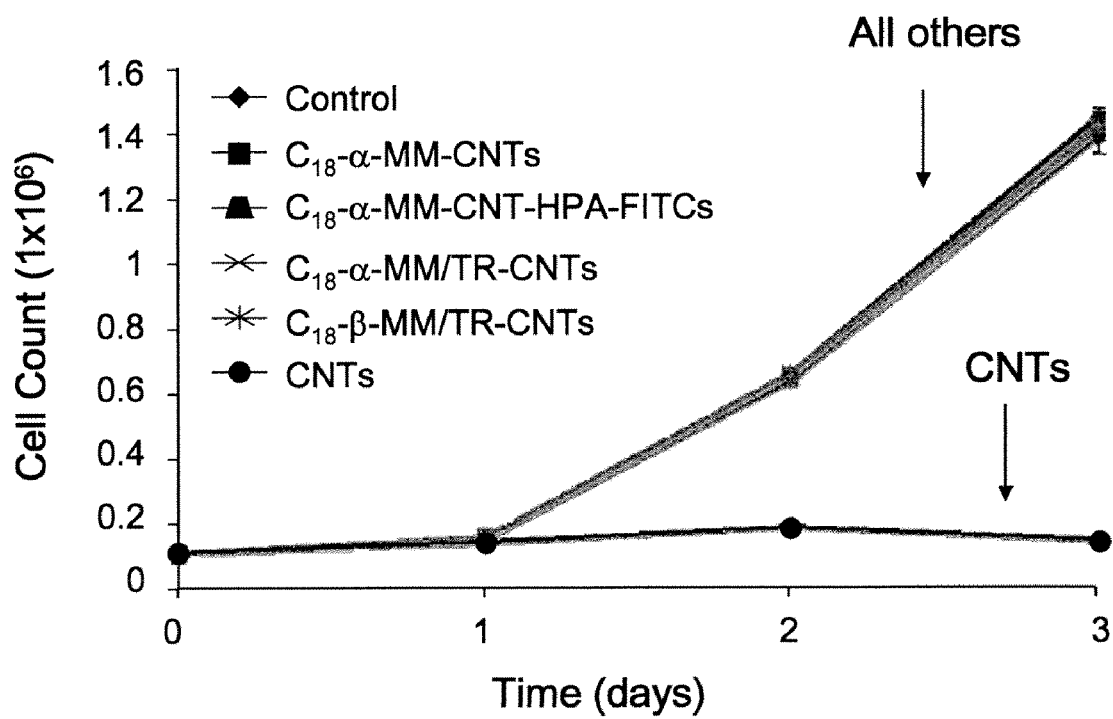
Fig. 4A-B

5A
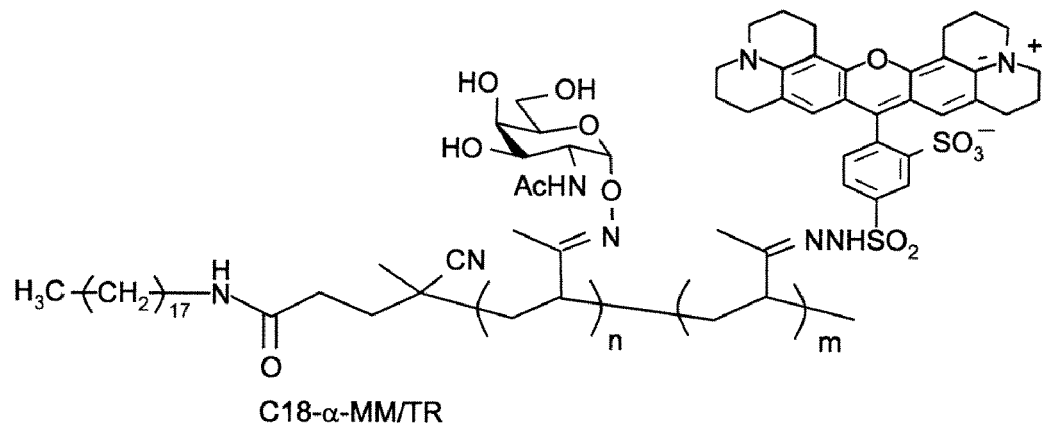
C18-α-MM/TR
5B
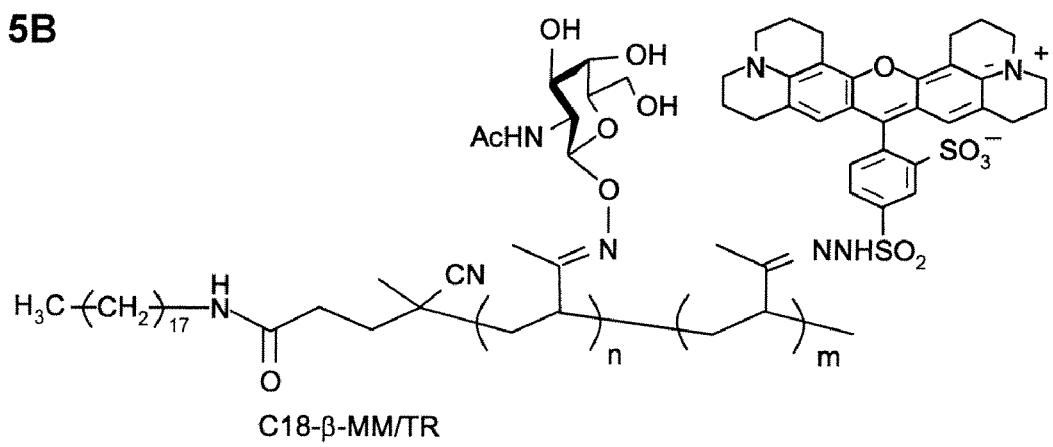
C18-β-MM/TR
Fig. 5A-B

7A
Synthesis of $C_{18}$-tailed initiator ($C_{18}$-ACPA):
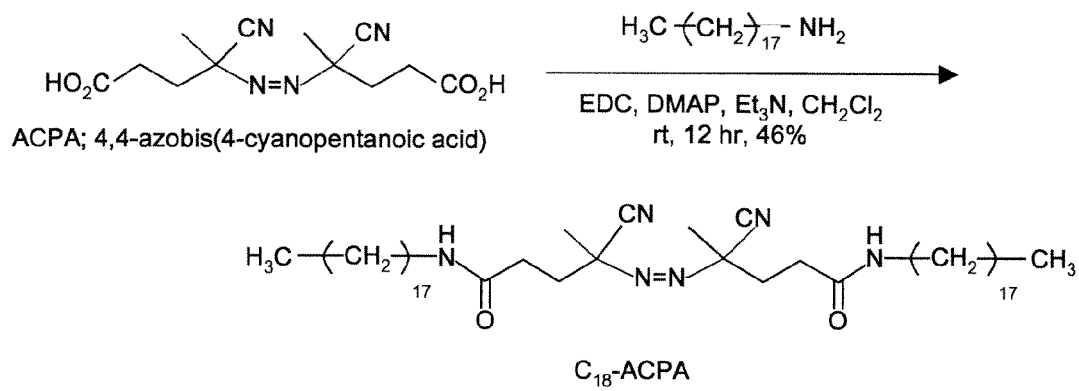
7B
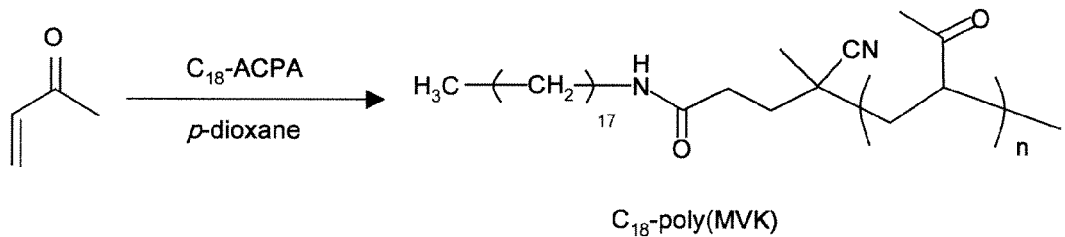
Fig. 7A-B

INTERFACING NANOSTRUCTURES TO BIOLOGICAL CELLS

CROSS-REFERENCE TO RELATED APPLICATIONS

This application claims priority from U.S. Provisional Patent Application No. 60/902,408 filed on Feb. 21, 2007, which is hereby incorporated by reference in its entirety.

STATEMENT OF GOVERNMENTAL SUPPORT

This invention was made with U.S. Government support under Contract Number DE-AC02-05CH11231 between the U.S. Department of Energy and The Regents of the University of California for the management and operation of the Lawrence Berkeley National Laboratory. The U.S. Government has certain rights in this invention.

REFERENCE TO SEQUENCE LISTING, COMPUTER PROGRAM, OR COMPACT DISK

None

BACKGROUND OF THE INVENTION

1. Field of the Invention

The present invention relates to the field of nanostructures, such as carbon nanotubes or other fullerenes, and also to the field of glycobiology.

2. Related Art

INTRODUCTION

Nanotechnology has infiltrated the field of cell biology in the form of quantum dots, nanofibers, and carbon nanotubes (CNTs), with applications ranging from imaging to tissue engineering[1-4]. Because of their scale and unique physical properties, these nanomaterials offer great opportunities for studying physiology at the level of single cells[5]. CNTs have attracted considerable attention due to their remarkable structural, electrical, and mechanical properties[6]. CNTs have been used to fabricate nanoscale sensors for detection of proteins[7] or carbohydrates[8]. Their unique near-infrared fluorescent properties might be exploited for biological sensing[9-11] and cancer therapy[12]. Several groups have shown that various cell types can engulf CNTs, suggesting their potential as delivery vehicles for biologically active cargo[10, 13-15]. These applications, however, have relied upon non-specific interaction between CNTs and cell surfaces, which precludes targeting to a particular cell type within a mixed population, or to a specific organelle within a cell. Moreover, the inherent cytotoxicity of CNTs has imposed severe limitations on their use in biological systems[16-18]. New strategies for controlling the interaction between CNTs and cells, and for curbing their toxicity, will be required in order to realize their full potential. Described below are processes including the coating of CNTs with a biomimetic polymer designed to mimic cell surface mucin glycoproteins. The functionalized CNTs were then bound to cell surfaces via specific carbohydrate receptors. Whereas unmodified CNTs induced cell death, the functionalized CNTs were found to be nontoxic. This approach for interfacing CNTs with cells should accelerate their use in biological systems.

SPECIFIC PATENTS AND PUBLICATIONS

Chen, et al., "Biomimetic Engineering of Carbon Nanotubes by Using Cell Surface Mucin Mimics," *Angew. Chem. Int. Ed.*, 2004, 6112-6116, disclose the preparation of a mucin mimic as shown in FIG. 2(a) of the present application, i.e., a synthetic mucin mimic in which α-GalNAc (N-acetylglucosamine) residues were linked through an oxime bond to a poly(methyl vinyl ketone) [poly(MVK)] backbone. The synthesis involved chemoselective ligation of poly(MVK) with an aminooxy-functionalized GalNAc analogue. The authors (who include the present inventors) introduced a $C_{18}$ lipid at one end of a mucin mimic polymer with a molecular weight of about 75000 g mol$^{-1}$ to enable surface modification of CNTs (carbon nanotubes). This paper further reports that the authors incubated $C_{18}$-α-MM-SWNTs with a solution of the lectin *Helix pomatia* agglutinin (HPA) conjugated with fluorescein isothiocyanate (HPA-FITC). Binding of the $C_{18}$-α-MM-SWNTs to the HPA lectin in a cell free environment was shown. However, this paper does not disclose the use of mucin mimic nanostructures for binding to a cell, nor does it suggest lectin glycosylation recognition.

Chen et al., "Interfacing Carbon Nanotubes with Living Cells," *J. Am. Chem. Soc.*, 128 (19), 6292-6293, 2006 Web Release Date: Apr. 21, 2006, whose authors include the present inventor, discloses certain aspects of the present invention.

U.S. Pat. No. 6,821,730, issued Nov. 23, 2004, entitled "Carbon nanotube molecular labels," discloses that labeled carbon nanotubes may be used to detect a variety of analytes.

Liu, "Modifications of carbon nanotubes with polymers," *European Polymer Journal*, Volume 41, Issue 11, November 2005, Pages 2693-2703, discloses that SWNTs may be non-covalently associated with a variety of linear polymers such as polyvinyl pyrrolidone (PVP) and polystyrene sulfonate (PSS).

G. R. Dieckmann, A. B. Dalton, P. A. Johnson, J. Razal, J. Chen and G. M. Giordano et al., *J Am Chem Soc* 125 (2003), pp. 1270-1277 disclose that an amphiphilic α-helical peptide had been successfully used to coat and solubilize carbon nanotubes.

A. Star, D. W. Steuerman, J. R. Heath and J. F. Stoddart, *Angew Chem Int Ed* 41, (2002), pp. 2508-2512 disclose that starch-wrapped SWNTs had been successfully prepared by the dispersion of SWNTs into an aqueous solution of starch/iodine complex by mild ultrasonication Kitano et al., "Functionalization of single-walled carbon nanotube by the covalent modification with polymer chains," *Journal of Colloid and Interface Science*, 1 Feb. 2007, Volume 306, Issue 1, Pages 28-33 (available on line 24 Oct. 2006) discloses that a single-walled carbon nanotube (SWNT), which had been oxidized by incubation with a mixture of nitric acid and sulfuric acid to afford carboxyl groups at its ends, was incubated with an azo-type radical initiator carrying poly(2-methacryloyloxyethyl d-glucopyranoside) blocks at both ends (PMEGlc-initiator).

Matsuura et al., "Lectin-mediated Supramolecular Junctions of Galactose-derivatized Single-walled Carbon Nanotubes," *Chemistry Letters*, 2003, Vol. 32, No. 3, p. 212 discloses a β-Galactoside-modified single-walled carbon nanotube (Gal-SWNT). Its solubility in water is increased by adsorption of lectin molecules on the sidewalls and supramolecular junctions are formed in the presence of galactose-specific lectins.

BRIEF SUMMARY OF THE INVENTION

The following brief summary is not intended to include all features and aspects of the present invention, nor does it imply that the invention must include all features and aspects discussed in this summary.

The present invention comprises the preparation of a biological complex, i.e., a cell or extracellular matrix in a tissue complexed in a non-covalent manner through biological recognition mechanisms to a nanostructure, e.g., a carbon nanotube, which has been functionalized with a sugar-containing material, i.e., glycosylated. The biological complex comprises this tissue, which will have a surface lectin or a glycosylated surface molecule, and a glycosylated nanostructure bound to said surface lectin or bound through an exogenous lectin to said glycosylated surface molecule. That is, a third component in the form of a lectin may be added to the complex, or the complex may be directed to an endogenous lectin in the biological material. The recognition between lectin and sugar on the nanostructure results in specific recognition and binding, based on the natural affinity for specific lectins and their counterpart glycosylation patterns. As illustrated in FIG. 1, the lectin 16 must recognize both the glycosylated nanostructure and a sugar on the cell or matrix surface. The tissue may comprise a mammalian cell, such as a human cell, an extracellular matrix, or other types of cells, such as plant or lower animal. In certain aspects of the invention, the cell is a breast cancer cell, an epithelial cell or a blood cell. The glycosylated nanostructure may be formed of a variety of sugars, depending on the target tissue. The glycosylated nanostructure, for example, may comprise a sugar that is GalNac, Gal 1, Fuc, and GLcNAc 1, or mixtures thereof. The glycosylated nanostructure may be synthesized as repeating units with sugars on every unit, which may be regarded as a mucin mimic comprising an aliphatic portion and a portion having repeated sugar-bearing units. The aliphatic portion is used to bind to the carbon nanostructure, since both may be hydrophobic. The glycosylated nanostructure in this case (and other cases) will have adsorbed thereto a synthetic polysaccharide.

In certain aspects of the invention, the synthetic polysaccharide comprises a lipid portion adsorbed thereto and selected from the group consisting of: linear polyethylene (i.e., alkyl), polypropylene, polyvinylpyrrolidone (PVP), polystyrene sulfonate (PSS), poly{(m-phenylenevinylene)-co-[(2,5-dioctyloxy-p-phenylene)vinylene]}(PmPV), poly{(2,6-pyridinylenevinylene)-co-[(2,5-dioctyloxy-p-phenylene)vinylene]}(PPyPV), poly{(5-alkoxy-m-phenylenevinylene)-co-[(2,5-dioctyloxy-p-phenylene)vinylene]}(PAmPV), and polystyrene.

In certain embodiments, the targeted glycosylated surface molecule is the same as the sugar on the glycosylated nanostructure. An example is N-acetyl galactosamine (GalNac).

In certain aspects of the invention, the complex will comprise a label. This may be a fluorescent dye or other label. It will serve to label and study the tissue being studied, and can characterize the number and type of extracellular glycosylation.

In certain aspects, the invention comprises the use of an exogenous lectin. In some cases, it is contemplated that an endogenous lectin can be used, such as a lectin on a cell surface or extracellular matrix. The lectin may be may be a C-type lectin, cluster of differentiation-22 (CD22) or asialoglycoprotein receptor (ASGPR), as further described below. For example, if the lectin CD22, present on B cells, were targeted, the glycosylated nanostructure would be prepared with 2-6-linked sialic acid residues.

In certain aspects, the present invention comprises a formulation for administration to a cell. The glycosylated nanostructure may comprise a sugar selected from the group consisting of at least one of GalNac, Gal1, Fuc, and GLcNAc1, and it will be in a sterile aqueous suspension for administration to a cell. The formulation may further comprise a lectin bound to the polysaccharide. A wide variety of lectins may be used, such as those listed in Table 1, Table 2 or Table 3.

In certain aspects, the invention also comprises a method of forming a complex comprising a glycosylated nanostructure on a living cell surface. It has been found that the present nanostructures, with lectin, are non-toxic to mammalian cells. The lectin may be administered separately from the complex, or it may be bound to the complex prior to administration. In either case, it will result in non-covalent cross-linking between the glycosylated nanostructure and the cell surface.

In certain aspects, the present invention provides a method for labeling cells based on their glycosylation or lectin recognition. One prepares a complex comprising a nanostructure and a labeled lipid-polysaccharide, or other glycosylated nanostructure, and contacts the cells with the complex, whereby the polysaccharide binds specifically to a lectin on a cell surface and labels the cells. The cells may be in vivo or in culture. As described, one may use a lectin either by pre-incubating the complex and binding a lectin to the complex prior to contacting the cells with the complex, or by pre-incubating the cells with the lectin.

BRIEF DESCRIPTION OF THE DRAWINGS

FIGS. 1A and B is a diagram of the present biological complexes, comprising glycosylated nanostructures and a biological tissue, which is a cell, and the use of lectins;

FIG. 3A is a fluorescence micrograph of CHO cells labeled with FITC-HPA-conjugated $C_{18}$-α-MM-coated CNTs; FIG. 3B is a bar graph of a flow cytometry analysis of the cells in FIG. 4a treated with various doses of modified CNTs. MFI=mean fluorescence intensity. Error bars represent the standard deviation for three replicates;

FIG. 4A is a bar graph of flow cytometry analysis of cells in pathway II of FIG. 3B: Row I shows the specific binding of $C_{18}$-α-MM/TR-CNTs (mucin mimic/Texas Red) to CHO cells coated with HPA; Row II shows no binding of $C_{18}$-α-MM/TR-CNTs to cells in the absence of HPA; Row III shows that $C_{18}$-α-MM/TR-CNTs do not bind CHO cells coated with HPA receptors. These data are representative of results observed in triplicate experiments. FIG. 4B is a graph which shows effects of glycopolymer-coated and unmodified CNTs on the growth of CHO cells. Similar results were obtained for Jurkat cells. Error bars represent the standard deviation for three replicates;

FIG. 5 is a drawing of a structure of $C_{18}$-α-MM polymer (top) and $C_{18}$—O-MM polymer (bottom) in which about 3% of the GanNac residues were replaced by the fluorescent dye Texas Red;

FIG. 6 is a bar graph showing HPA-FITC binding to CHO cells at various concentrations; and FIG. 7A-C is a schematic representation of certain synthetic steps used in the preparation of the C18-α-MM polymer of FIG. 5.

DETAILED DESCRIPTION OF THE PREFERRED EMBODIMENT

Definitions

Except to the extent defined otherwise, all technical and scientific terms used herein have the same meaning as commonly understood by one of ordinary skill in the art.

The term "nanostructure" is used herein to mean a closed or hollow, discrete particle having a diameter less than 200 nanometers. A "nanotube" is a nanostructure having a length at least ten times its diameter. The nanostructure may exhibit optimum properties with a length between 10 micron and 10 nanometers and a diameter between 0.5 nm and 100 nm. A "nanostructure" as used herein is essentially atomically smooth, having mechanical defects essentially only at places where covalent attachment may be desired. The present nanostructure may contain a mixture of materials, or may be essentially pure, or contain dopants, e.g., carbon doped with Ge, B, P, As, Ge, Ga, In, or Al.

Figure 2A:
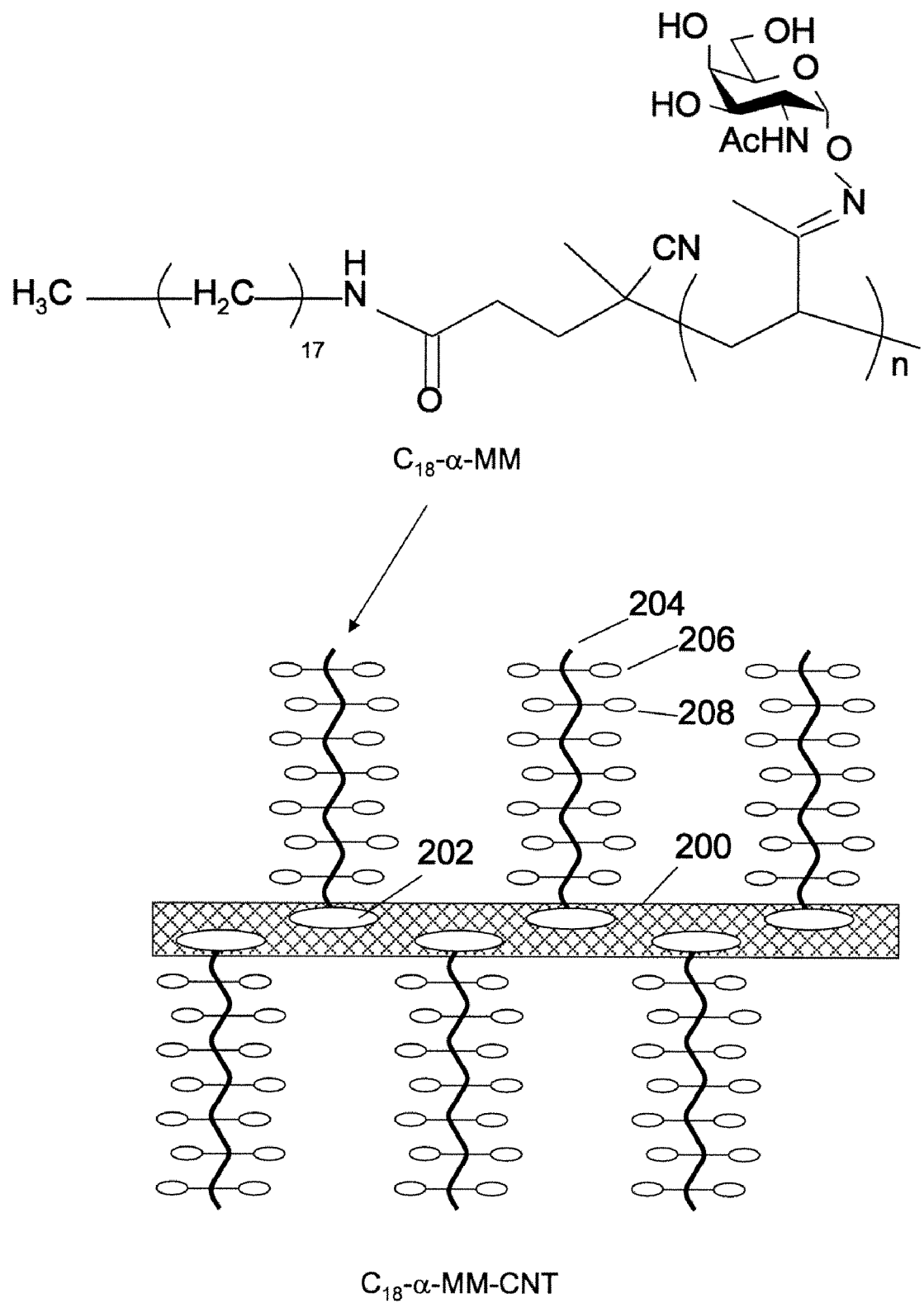
FIG. 2 is diagram showing the presently exemplified glycosylated nanostructure having a mucin mimic nanostructure (MMN), $C_{18}$-αMM-CNT (FIG. 2a) and two pathways, pathway I and pathway II for binding the MMN to cell surface glycoproteins (FIG. 2b)

The term "nanostructure" includes nanotubes, nanospheres, nanowires, nanorods, and nanodisks (see Gao et al., "Spiral Spin Order of Self-Assembled Co Nanodisk Arrays," *Phys. Rev. Lett.,* 2006, 96, 137205). In the case of non-elongated nanostructures, the length of the lipid portion, described below, may be shortened accordingly. The term "nanostructure" may further be defined to include a hexagonal network graphite plane, which may be rolled into a cylindrical shape. This graphitic nanostructure has an electron structure widely varied depending upon a tube diameter and a chiral angle The term "glycosylated nanostructure" means a nanostructure that is covalently or noncovalently bound to a carbohydrate. The carbohydrate may be a plurality of monosaccharides or a polysaccharide, such as a synthetic polysaccharide. The carbohydrate preferably comprises a lipid portion for noncovalent attachment to the nanostructure. Carbohydrates thus include substituted and unsubstituted monosaccharides, disaccharides, oligosaccharides, and polysaccharides. The saccharide can be an aldose or ketose, and may comprise 3, 4, 5, 6, or 7 carbons. In one embodiment the saccharide is a monosaccharide. In another embodiment the saccharides may be pyranose and furanose sugars. They can be optionally deoxygenated at any corresponding C-position, and/or substituted with one or more moieties such as hydrogen, halo, haloalkyl, carboxyl, acyl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, thioester, thioether, oxime, hydrazine, carbamate.

The term "glycosylated surface molecule" means a cell surface or an extracellular matrix component available for binding to an exogenous agent (lectin), which in this case will be attached to the nanostructure in forming a cellular complex. The major groups of glycosylated molecules are the glycoproteins, glycopeptides, peptidoglycans, glycolipids and lipopolysaccharides. Glycoproteins are covalently bound to sugars, which include galactose, glucose, mannose, N-acetylneuraminic acid (NANA or sialic acid), fucose, N-acetylgalactosamine, N-acetylglucosamine, and xylose. The unique "fingerprint" of each glycoprotein is conferred by the number and arrangement of these sugars.

The present glycoproteins may have sugars (e.g., monosaccharides) attached to either the nitrogen on asparagine (N-linked) or sugars attached to the oxygen on serine or threonine (O-linked).

The present glycosylated cell surface molecules include glycolipids, e.g., major components of nervous and brain tissue, and further include glycoproteins in the form of proteoglycans, which comprise a major component of the extracellular matrix. Proteoglycan molecules contain both protein and glycosaminoglycans, which are a type of polysaccharide. Proteoglycans are found in cartilage and other connective tissues. Their reactive saccharide chains bind cell adhesion molecules and growth factors. The heparan sulfate proteoglycans are believed to play an important role in the intercellular communication required for neuronal development.

The term "synthetic polysaccharide" includes lipid, polymer, or peptide backbones, to which is attached mono- or oligosaccharides pendant to the backbone. These include isolated mucins, and "mucin mimics." A variety of synthetic polymers may be adapted for use with the present nanostructures. A generic formula may be used to illustrate this:

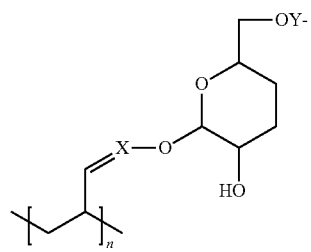

Where n represents from about 5-30 repeating units, X may be a direct bond (i.e., eliminating the double bond whereby the oxygen is bonded directly to the backbone carbon), N or S and is linked to a mono, di- or tri-sachharide, where Y— is H in the case of a monosaccharide and a linkage to another saccharide unit in the case of a polysaccharide. Thus, "n" in FIG. 5 is about 5-30.

The term "mucin" means a high molecular mass glycoprotein in which proline and serine constitute up to 20-55% of the total amino acids and are concentrated in one or several regions of the polypeptide. In this case, the units represented in brackets above are amino acids, in the case of native mucin. The serine/threonine residues are heavily glycosylated, and 40-80% of the mass of such mucins consists of)-linked oligosaccharides. The cysteines at the N- and C-ends may link mucin monomers by disulfide bridges. A "mucin mimic" is a mucin-like molecule which does not occur in nature, is heavily glycosylated, and has at least one monosaccharide of a type found in native mucin.

The term "lectin" means a non-antibody compound, which binds to specific carbohydrates, such as glycosylated biological molecule, or as taught here, a glycosylated nanostructure. Because of their ability to recognize complex carbohydrates on cell surfaces with high specificity, lectins are proteins that play important roles in the social life of cells. Examples of invertebrate lectins include the recognition of "sister" cells as part of the aggregation mechanisms in primitive organisms (e.g., slime molds, sponges and corals), the specific binding of polysaccharide-coated pathogenic bacteria in the innate immunity system of invertebrates, and the mediation of symbiosis, for example between coral and their symbiotic algae. See, Sanchez et al., Biochemical and Structural Analysis of *Helix pomatia* Agglutinin A Hexameric Lectin with a Novel Fold," *Biol. Chem.,* Vol. 281, Issue 29, 20171-20180, Jul. 21, 2006.

Preferred lectins are polyvalent, meaning that they bind more than one sugar molecule, and, in the present methods and materials serve to effectively cross link a sugar on a nanostructure to a sugar on a cell. However, lectin may be synthesized directly on the nanostructure in multiple copies and bind to cellular molecules.

Included in the present definition is the exemplified lectin, HPA. As reported in Brooks, "The involvement of *Helix pomatia* lectin (HPA) binding N-acetylgalactosamine glycans in cancer progression," *Histol Histopathol,* 2000 January; 15(1): 143-58, a large number of lectin histochemical studies have demonstrated that expression of HPA-binding glycoproteins by cancer cells to be a marker of metastatic competence and poor prognosis in a range of common human adenocarcinomas, including those of breast, stomach, ovary, esophagus, colorectum, thyroid and prostate. Around 80% of metastases arising from primary breast cancer are predictably HPA positive. The nucleotide sequence of HPA was deposited in the GenBank™ data bank with accession number DQ341310. As further reported in Sanchez et al., supra, HPA has been shown to agglutinate blood group A red cells, but not those of blood groups B or O. The binding preference was established to be Forssman antigen (GalNAc1-3GalNAc-R) >blood group A substance (GalNAc1-3[Fuc1-2]Gal]>Tn antigen (GalNAc-Ser/Thr)>GalNAc>GlcNAc, therefore confirming the specificity for terminal —N-acetyl-D-galactosamine (GalNAc) residues.

For purposes of further defining the lectin HPA, Brooks et al., "N-acetylgalactosamine, N-acetylglucosamine and sialic acid expression in primary breast cancers," *Acta Histochemica* 103(1): 2001, Pages 37-51 describes work elaborating on the fact that that *Helix pomatia* (HPA) recognizes N-acetylgalactosamine and N-acetylglucosamine glycans. In this study, 111 primary breast cancers were assessed for binding of HPA and labeling characteristics were compared directly with those of *Dolichos biflorus* agglutinin and soybean agglutinin, both of which also recognize N-acetylgalactosamine, *Griffonia simplicifolia* agglutinin II, which recognizes N-acetylglucosamine, and *Limax flavus* agglutinin, *Sambucus nigra* agglutinin and *Maackia amurensis* lectin I, all of which recognize sialic acids. Results indicate that the HPA-binding partners expressed by cancer cells are predominantly N-acetylgalactosamine glycans, but some recognition of N-acetylglucosamine species is also likely.

Thus the use of HPA is an example of a lectin which specifically binds only to certain types of cells.

Also included in the present definition are lectins which bind to certain tissues, bearing carbohydrates in an extracellular environment. An example is found in Kagayama et al., "Lectin binding in bone matrix of adult rats with special reference to cement lines," *Tohoku J Exp Med*. 1993 June; 170(2):81-91. The authors found that glycoconjugates recognized by four lectins (LFA, MPA, WGA, and ConA) were found in adult rat bone. LFA, a lectin recognizing sialic acid, stained intensely the cement lines of calvariae and the interface between cartilage and bone of mandibular condyles, which were also stained with WGA, and intermittently stained with ConA. Schünke et al., "Lectin-binding in normal and fibrillated articular cartilage of human patellae," *Virchows Archiv* 407(2) 221-231 (1985) disclose that normal articular cartilage reveals lectin binding-sites for Concanavalin A (Con A) and wheat germ agglutinin (WGA), but not for soybean agglutinin (SBA), peanut agglutinin (PNA) and *Ulex europaeus* agglutinin (UEA). In fibrillated cartilage the distribution pattern of Con A and WGA is completely changed.

The term "lipid" means an alky group, preferably 10-30 carbons in length.

The term "alkyl" means a branched or unbranched, saturated or unsaturated acyclic hydrocarbon radical. Suitable alkyl radicals include, for example, methyl, ethyl, n-propyl, i-propyl, 2-propenyl (or allyl), vinyl, n-butyl, t-butyl, i-butyl (or 2-methylpropyl), etc. In particular embodiments, alkyls have between 1 and 20 carbon atoms, between 1 and 10 carbon atoms or between 1 and 5 carbon atoms. The term alkyl includes heteroalkyl, as defined below, "substituted alkyl," which refers to an alkyl as just described in which one or more hydrogen atom bound to any carbon of the alkyl is replaced by another group such as a halogen, aryl, substituted aryl, cycloalkyl, substituted cycloalkyl, heterocycloalkyl, substituted heterocycloalkyl, halogen, alkylhalos (e.g., $CF_3$), hydroxy, phosphido, alkoxy, amino, thio, nitro, and combinations thereof. Suitable substituted alkyls include, for example, benzyl, trifluoromethyl and the like.

The term "heteroalkyl" means an alkyl as described above in which one or more carbon atoms to any carbon of the alkyl is replaced by a heteroatom selected from the group consisting of N, O, P, B, S, Si, Sb, Al, Sn, As, Se and Ge. This same list of heteroatoms is useful throughout this specification. The bond between the carbon atom and the heteroatom may be saturated or unsaturated. Thus, an alkyl substituted with a heterocycloalkyl, substituted heterocycloalkyl, heteroaryl, substituted heteroaryl, alkoxy, aryloxy, boryl, phosphino, amino, silyl, thio, or seleno is within the scope of the term heteroalkyl. Suitable heteroalkyls include cyano, benzoyl, 2-pyridyl, 2-furyl and the like.

The term "aryl" means an aromatic substituent, which may be a single aromatic ring or multiple aromatic rings that are fused together, linked covalently, or linked to a common group such as a methylene or ethylene moiety. The aromatic ring(s) may include phenyl, naphthyl, anthracenyl, and biphenyl, among others. In particular embodiments, aryls have between 1 and 200 carbon atoms, between 1 and 50 carbon atoms or between 1 and 20 carbon atoms, including "substituted aryl," which refers to aryl as just described in which one or more hydrogen atom bound to any carbon is replaced by one or more functional groups such as alkyl, substituted alkyl, cycloalkyl, substituted cycloalkyl, heterocycloalkyl, substituted heterocycloalkyl, halogen, alkylhalos (e.g., $CF_3$), hydroxy, amino, phosphido, alkoxy, amino, thio, nitro, and both saturated and unsaturated cyclic hydrocarbons which are fused to the aromatic ring(s), linked covalently or linked to a common group such as a methylene or ethylene moiety. The common linking group may also be a carbonyl as in benzophenone or oxygen as in diphenylether or nitrogen in diphenylamine.

The term aryl includes "heteroaryl," which refers to aromatic or unsaturated rings in which one or more carbon atoms of the aromatic ring(s) are replaced by a heteroatom(s) such as nitrogen, oxygen, boron, selenium, phosphorus, silicon or sulfur. Heteroaryl refers to structures that may be a single aromatic ring, multiple aromatic ring(s), or one or more aromatic rings coupled to one or more non-aromatic ring(s). In structures having multiple rings, the rings can be fused together, linked covalently, or linked to a common group such as a methylene or ethylene moiety. The common linking group may also be a carbonyl as in phenyl pyridyl ketone. As used herein, rings such as thiophene, pyridine, isoxazole, pyrazole, pyrrole, furan, etc. or benzo-fused analogues of these rings are defined by the term "heteroaryl."

"Substituted heteroaryl," included in heteroaryl as just described including in which one or more hydrogen atoms bound to any atom of the heteroaryl moiety is replaced by another group such as a halogen, alkyl, substituted alkyl, aryl, substituted aryl, heteroaryl, substituted heteroaryl, alkoxy, aryloxy, boryl, phosphino, amino, silyl, thio, seleno and combinations thereof. Suitable substituted heteroaryl radicals include, for example, 4-N,N-dimethylaminopyridine.

Overview

Described below are methods and materials in which the interface between nanostructures, which can mimic glycans, was modified so as to reflect physiological interactions at the cell periphery. Glycans are major determinants of molecular recognition on the cell surface. They participate in diverse processes such as pathogen binding, cell trafficking, endocytosis and modulation of cell signaling[19]. Glycan structures vary as a function of cell type and physiological state[20], and discrete epitopes are associated with specific organelles[21]. Thus, CNTs or other nanostructures that are functionalized to engage in glycan-receptor interactions are ideal substrates for more refined applications in cell biology.

We previously demonstrated that CNTs can be coated with glycopolymers that mimic cell surface mucin glycoproteins[22]. This work did not address binding of this material to cellular or tissue surfaces. In contrast, the present invention is related to the use of such agents in binding to selected tissue and cells, especially living cells, and to novel compositions relating to such uses.

Described below is a strategy for interfacing biocompatible CNTs with cell surfaces by virtue of carbohydrate-receptor interactions. The synthetic methods used to produce the glycopolymers permit the facile introduction of myriad alternative ligands, in addition to sugars, that could encode interactions with numerous receptor types. This strategy may offer new opportunities for probing biological processes. Experimental and theoretical studies have indicated that the immediate nanotube environment can influence CNT properties. For example, charge transfer to the CNT from attached chemical species can alter the electrical conductance, and mechanical properties are altered by changes in moments and local bonding structure. Therefore, it is likely that local conditions around a cell might be monitored by changes in the electrical, mechanical, or optical properties of CNTs as they respond to different environments.

As shown in FIG. 1, the present glycosylated nanostructures comprise an inert nanostructure 10, shown as having a repeating hexagonal carbon structure, and which is hydrophobic, to which is non-covalently attached a hydrophobic linking group 12 (e.g., lipid), designed to bind to the nanostructure. The linking group 12 is covalently bound to a sugar portion 14, which contains a number of saccharide units. Lectins 16 are non-covalently complexed either to the sugar 14 (FIG. 1A) or to a cell surface molecule 20 (FIG. 1B). The lectin 16 is multivalent, meaning that it binds more than one sugar group, thereby causing a biological complex to form between the saccharide-containing molecule 20 of cell 18 and the glycosylated nanostructure. In addition, the glycosylated nanostructure may contain a label 22, preferably attached to the linking group 12. In addition, in certain cell types, the lectin 16 is inherently present on the cell surface as in FIG. 1B. In this case, the glycosylated nanostructure is bound directly to the endogenous cell surface lectin. A separate cell surface (or tissue) glycan is not necessary. The distinction may be somewhat arbitrary in that the same surface glycoprotein may have a lectin protein domain, as well as a particular glycosylation pattern. For example, selectins are considered to have a lectin domain. See, also, Schoeppner H L, Raz A, Ho S B, Bresalier R. S., "Expression of an endogenous galactose-binding lectin correlates with neoplastic progression in the colon," *Cancer* 1995; 75:2818-2826. Granulocytes are known to express cell surface lectins, as are other blood cells. Raz et al., "Differential Expression of Endogenous Lectins on the Surface of non-tumorigenic, Tumorigenic and Metastatic Cells," *Cancer Res.* 46(7): 3667-3672 (1986) describes the expression of a galactoside (galactose) specific lectin. The expression of this lectin was increased in malignant cells. Thus, according to the present methods, a glycosylated nanostructure contacted with cells with possible malignancy would give higher binding percentage and overall avidity with malignant cells. In this method, no exogenous lectin is used.

Sugar portion 14 may be a variety of mono- and oligosaccharides. These may be synthesized by a variety of methods. See, Sears et al., "Toward Automated Synthesis of Oligosaccharides and Glycoproteins," *Science* 23 Mar. 2001: Vol. 291. no. 5512, pp. 2344-2350, and Zhang et al., "A New Strategy for the Synthesis of Glycoproteins," *Science* 16 Jan. 2004: Vol. 303. no. 5656, pp. 371-373. The example below describes the incorporation of GalNac-modified serine into a polypeptide chain in an *E. coli* system. Thus one may use in the present methods selective recognition by a GlcNAc-specific lectin, in binding to a GlcNAc-specific lectin, Bandeiraea simplicifolia II (BSII), to wild-type myoglobin and to glycomyoglobin. Marschal, et al., "Sequence and Specificity of a Soluble Lactose-binding Lectin from *Xenopus laevis* Skin," *JBC* 267(18) 2942-12949 (1992) disclose a variety of lectins that have homology to *Xenopus* lectins.

In addition, various lectins may be designed using combinatorial chemistry. Blixt et al., "Printed covalent glycan array for ligand profiling of diverse glycan binding proteins," PNAS (49): 17033-17038 (2004) describes a glycan microarray which comprises 200 synthetic and natural glycan sequences representing major glycan structures of glycoproteins and glycolipids. The glycans can be used for analysis of GBP (Glycan binding protein) specificity. Given the present teachings, one may adapt for use the C-type lectins, siglecs, and galectins as studied in the above-referenced paper. This includes a lectin termed DC-SIGN, a member of the group 2 subfamily of the C-type lectin family, which is a dendritic cell protein implicated in innate immunity and the pathogenicity of HIV-1. The DC-SIGN-Fc lectin may be used for specific recognition of two classes of glycans, various fucosylated oligosaccharides with the Fuc1-3GlcNAc and Fuc1-4GlcNAc oligosaccharides found as terminal sequences on N- and O-linked oligosaccharides, and mannose-containing oligosaccharides terminated with Man1-2-residues. An example of a lectin-like interaction demonstrated by the work in the above paper involves influenza virus hemagglutinin (HA). HA recognizes sialosides as cell surface receptor determinants through the viral binding protein, the hemagglutinin. Depending on the species of origin, the hemagglutinin has specificity for sialosides with sialic acid in the NeuAc2-3Gal or NeuAc2-6Gal linkage. While the intrinsic affinity of sialosides for the hemagglutinin is weak (Kd 2 mM), binding is strengthened through polyvalent interactions at the cell surface.

In certain embodiments, the lectin may be present on the cell surface to be targeted, and therefore, no exogenous need be added to the complex. Again referring to FIG. 1B, in this case a cell 24 bears lectin 16, which is recognized by the sugar 14 on the glycosylated nanostructure itself. That is, a cell surface lectin is specifically targeted by the glycosylated nanostructure.

Formulations

The present glycosylated nanostructures, with or without lectins, may be suspended by sonication, as described above. In addition, one may prepare suspensions for administration to cells in vivo or in culture, and, accordingly, formulations of the present invention may comprise a preservative, suspending agent, wetting agent, tonicity agent and/or diluent. In one embodiment, the formulations provided herein may comprise from about 0.01% to about 95%, or about 0.01% to about 50%, or about 0.01% to about 25%, or about 0.01% to about 10%, or about 0.01% to about 5% of one or more pharmacologically suitable suspending fluids which is physiologically acceptable upon administration. Pharmacologically suitable fluids for use herein include, but are not limited to, polar solvents, including, but not limited to, compounds that contain hydroxyl groups or other polar groups. Solvents include, but are not limited to, water or alcohols, such as ethanol, isopropanol, and glycols including propylene glycol, polyethylene glycol, polypropylene glycol, glycol ether, glycerol and polyoxyethylene alcohols. Polar solvents also include protic solvents, including, but not limited to, water, aqueous saline solutions with one or more pharmaceutically acceptable salt(s), alcohols, glycols or a mixture there of. In one alternative embodiment, the water for use in the present formulations should meet or exceed the applicable regulatory requirements for use in drugs.

In certain embodiments herein, the formulations of the present invention have a pH of about 2.0 to about 9.0. Optionally, the formulations of the present invention may contain a pH buffer. For example, a buffer may comprise any known pharmacologically suitable buffers, which are physiologically acceptable upon administration. The buffer may be added to maintain the pH of the formulation between about 3.0 and about 7.0, for example.

Sterility or adequate antimicrobial preservation may be provided as part of the present formulations. Since certain formulations of the present invention are intended to be administered to cells, it is preferred that they be free of pathogenic organisms. A benefit of a sterile liquid suspension is that it reduces the possibility of introducing contaminants into a culture or individual when the suspension formulation is administered. Processes that may be considered for achieving sterility may include any appropriate sterilization steps known in the art.

In one embodiment, the formulation of the present invention is produced under sterile conditions, and the sonication of the glyconanostructure is performed in a sterile environment, and the mixing and packaging is conducted under sterile conditions. In one alternative embodiment, one or more ingredients in the present formulation may be sterilized by steam, gamma radiation or prepared using or mixing sterile steroidal powder and other sterile ingredients where appropriate. Also, the formulations may be prepared and handled under sterile conditions, or may be sterilized before or after packaging.

In addition to or in lieu of sterilization, the formulations of the present invention may contain a pharmaceutically acceptable preservative to minimize the possibility of microbial contamination. Additionally, a pharmaceutically-acceptable preservative may be used in the present formulations to increase the stability of the formulations. It should be noted, however, that any preservative must be chosen for safety, as the treated cells or tissues may be sensitive to irritants. Preservatives suitable for use herein include, but are not limited to, those that protect the solution from contamination with pathogenic particles, including phenylethyl alcohol, benzalkonium chloride, benzoic acid, or benzoates such as sodium benzoate. Preferably, the preservative for use in the present formulations is benzalkonium chloride or phenylethyl alcohol. In certain embodiments, the formulations herein comprise from about 0.01% and about 1.0% w/w of benzalkonium chloride, or from about 0.01% and about 1% v/w phenylethyl alcohol. Preserving agents may also be present in an amount from about 0.01% to about 1%, preferably about 0.002% to about 0.02% by total weight or volume of the formulation.

The formulations provided herein may also optionally comprise from about 0.01% to about 90%, or about 0.01% to about 50%, or about 0.01% to about 25%, or about 0.01% to about 10%, or about 0.01% to about 1% w/w of one or more emulsifying agent, wetting agent or suspending agent.

Various Nanostructures

The CNTs (SWNTs) referred to below are merely exemplary. The term nanotube is used here in a broad sense to include single-walled nanotubes, multiwalled nanotubes, etc. Other forms of nanotube may be used, so long as they have uniform mechanical properties and are chemically inert to the extracellular environment. For example, BC2N or BN nanotubes, as described in Zettl, "Non-Carbon Nanotubes," Adv. Mat. 8(5):443-445 (1996). Gold, palladium and platinum nanotubes are also included. See, Yugang et al., "Metal nanostructures with hollow interiors," Advanced Materials, 2003, vol. 15, no 7-8, pp. 641-646.

The term nanotube particularly includes carbon nanotubes. These may consist of one tube of graphite, a one-atom thick single-wall nanotube (SWNT), or a number of concentric tubes called multiwalled nanotubes (MWNT). SWNTs, although predominantly having a single wall, are understood instances within a given sample of tubes having multiple walls in some cases. See, Flauhaut et al., "Synthesis of single-walled carbon nanotube-Co—MgO composite powders and extraction of the nanotubes," J. Mater. Chem. 2000, vol. 10, no 2, pp. 249-252.

SWNTs are produced by laser vaporization (LV), electric-arc vaporization (AV) and by chemical vapor deposition (CVD) (The LV and AV methods produce loose nanotubes, which are grown in the gas-phase from co-vaporized carbon and approximately 1% catalyst metal. CVD utilizes thermal decomposition of a mixture of carbon-containing and metal-catalyst-containing precursor gases (e.g., methane and ferrocene) above a hot substrate.

MWNTs for use in the present cellular complexes may be synthesized by the standard arc technique as described in Ebbesen et al., U.S. Pat. No. 5,641,466 issued Jun. 24, 1997, which describes a method for large-scale synthesis of carbon nanotube. These nanotubes have a near perfect carbon tubule structure that resembles a sheet of sp2 bonded carbon atoms rolled into a seamless tube. They are generally produced by one of three techniques, namely electric arc discharge, laser ablation and chemical vapor deposition. The arc discharge technique involves the generation of an electric arc between two graphite electrodes, one of which is usually filled with a catalyst metal powder (e.g., iron, nickel, cobalt), in a helium atmosphere. The laser ablation method uses a laser to evaporate a graphite target, which is usually filled with a catalyst metal powder too. The arc discharge and laser ablation techniques tend to produce an ensemble of carbonaceous material, which contain nanotubes (30-70%), amorphous carbon and carbon particles (usually closed-caged ones). The nanotubes must then be extracted by some form of purification process before being manipulated into place for specific applications. The chemical vapor deposition process utilizes nanoparticles of metal catalyst to react with a hydrocarbon gas at temperatures of 500-900° C. A variant of this is plasma enhanced chemical vapor deposition in which vertically aligned carbon nanotubes can easily be grown. In these chemical vapor deposition processes, the catalyst decomposes the hydrocarbon gas to produce carbon and hydrogen. The carbon dissolves into the particle and precipitates out from its circumference as the carbon nanotube. Thus, the catalyst acts as a 'template' from which the carbon nanotube is formed, and by controlling the catalyst size and reaction time, one can easily tailor the nanotube diameter and length respectively to suit. Carbon tubes, in contrast to a solid carbon filament, will tend to form when the catalyst particle is ~50 nm or less because if a filament of graphitic sheets were to form, it would contain an enormous percentage of 'edge' atoms in the structure. Alternatively, nanotubes may be prepared by catalytic pyrolysis of hydrocarbons as described by Endo, et al., in J. Phys. Chem. Solids, 54, 1841 (1993), or as described by Terrones, et al., in Nature, 388, 52 (1997) or by Kyotani, et al., in Chem. Mater., 8, 2190 (1996), the contents of all of which are incorporated by reference for describing nanotube preparation. Exemplary nanowires include aluminum, e.g., Ono et al., "Magnetic orderings in Al nanowires suspended between electrodes," Applied Physics Letters-Jun. 23, 2003-Volume 82, Issue 25, pp. 4570-4572; those described in Geng et al., "Synthesis and optical properties of S-doped ZnO nanowires," Synthesis and optical properties of S-doped ZnO nanowires," Applied Physics Letters-Jun. 30, 2003-Volume 82, Issue 26, pp. 4791-4793; "Self-assembled growth of epitaxial erbium disilicide nanowires on silicon (001)" by Yong Chen, Douglas A. A. Ohlberg, Gilberto Medeiros-Ribeiro, Y. Austin Chang, and R. Stanley Williams in Applied Physics Letters, 76, p. 4004, June 2000, and silicon nanowires as described in Englander et al., "Local synthesis of silicon nanowires and carbon nanotubes on microbridges," Applied Physics Letters-Jun. 30, 2003-Volume 82, Issue 26, pp. 4797-4799.

Nanorods may be carbon (see, e.g., Science 10 Sep. 1999: Vol. 285. no. 5434, pp. 1719-1722); metal oxide (see U.S. Pat. No. 6,036,774); silicon carbide (see U.S. Pat. No. 5,997,832); metals and metal alloys such as copper, nickel and gold, see e.g., Salem et al., "Multi-component nanorods for vaccination applications," Nanotechnology 16 484-487, 2005.

While the preferred embodiment as contemplated herein used quasi-one dimensional structures, the shape of the nanostructure is not important. Therefore, other nanostructures such as C60 fullerenes and semiconductor nanocrystals may be adsorbed on the present complexing agents.

The term "semiconductor nanocrystal" is defined in Weiss et al., U.S. Pat. Nos. 6,727,065 and 6,207,392. Generally, the term means an organic or inorganic crystal particle, preferably a single crystal particle, having an average cross-section no larger than about 20 nanometers (nm) or $20 \times 10^{-9}$ meters (200 Angstroms), preferably no larger than about 10 nm (100 Angstroms) and a minimum average cross-section of about 1 nm, although in some instances a smaller average cross-section nanocrystal, i.e., down to about 0.5 nm (5 Angstroms), may be acceptable. Typically the nanocrystal will have an average cross-section ranging in size from about 1 nm (10 Angstroms) to about 10 nm (100 angstroms). A nanometer crystal or nanocrystal of Group II-VI and/or Group III-V semiconductor compounds capable of emitting electromagnetic radiation upon excitation, although the use of Group IV semiconductors such as germanium or silicon, or the use of organic semiconductors, may be glycosylated as taught here and used as both a nanostructure and a label.

Various Lectins

Other GalNac-binding lectins besides HPA may be used, such as are described, for example in Yi et al., "Substructural specificity and polyvalent carbohydrate recognition by the *Entamoeba histolytica* and rat hepatic N-acetylgalactosamine/galactose lectins," *Glycobiology, Vol* 8, 1037-1043, 1998. As described there, both the *Entamoeba histolytica* lectin, a virulence factor for the causative agent of amebiasis, and the mammalian hepatic lectin bind to N-acetylgalactosamine (GalNAc) and galactose (Gal) nonreducing termini on oligosaccharides, with preference for GalNAc. As stated above, the lectin may be prepared as an isolated composition and added exogenously to the biological tissue, or, it may be found endogenously on the tissue to be complexed.

Another lectin of interest is the C-type lectin domain family. Members of the calcium-dependent (C-type) lectin family recognize carbohydrate chains and are involved in host defense mechanisms. See, e.g., Suzuki, et al., "Molecular cloning and expression of cDNA encoding human macrophage C-type lectin: its unique carbohydrate binding specificity for Tn antigen," *J. Immun.* 156: 128-135, 1996. Sequence analysis predicted that the 292-amino acid type II transmembrane protein has a cytoplasmic domain with a tyr-glu-asn-phe (YENF) internalization signal, a transmembrane domain, a neck domain, and a C-type lectin domain (also called a carbohydrate recognition domain, or CRD) containing a gln-pro-asp motif. Western blot and functional analyses indicated that the approximately 35-kD protein binds specifically to galactose or N-acetylgalactosamine in the presence of calcium.

A C-type lectin is described in Keshi et al., "Identification and Characterization of a Novel Human Collectin CL-K1," Microb. Imm. 50 (12) 1001-1013 (2006). Various types of collectins are there described. The sequence of CL-K1 is given there. Additional sequences may be found in GenBank, e.g., NP_989680 soluble mannose-binding lectin [*Gallus gallus*], and NP_989680, soluble mannose-binding lectin [*Gallus gallus*].

Another C-type lectin, hMGL, is described in Takada et al., "Human Macrophage C-Type Lectin Specific for Galactose and N-Acetylgalactosamine Promotes Filovirus Entry," *J. Virol.* 2004 March; 78(6): 2943-2947. The paper shows that human macrophage galactose- and N-acetylgalactosamine-specific C-type lectin (hMGL), whose ligand specificity differs from DC-SIGN and L-SIGN, also enhances the infectivity of filoviruses. An initial target of filovirus infection is the mononuclear phagocytic cell. Calcium-dependent (C-type) lectins such as dendritic cell- or liver/lymph node-specific ICAM-3 grabbing nonintegrin (DC-SIGN or L-SIGN, respectively), as well as the hepatic asialoglycoprotein receptor, bind to Ebola or Marburg virus glycoprotein (GP) and enhance the infectivity of these viruses in vitro. High-mannose N-glycans on the GP appear to be important for interaction with these lectins. This infectivity is thought to be related to human macrophage C-type lectins specific for galactose/N-acetylgalactosamine (hMGL). Although lectins on antigen-presenting cells potentially function as an endocytic receptor for antigen uptake, DC-SIGN, originally identified as an attachment factor for human immunodeficiency virus (HIV) gp120), has been thought to facilitate HIV entry into susceptible cells and to play a role in transferring infectious virus particles from dendritic cells to CD4/CCR5 type T cells. L-SIGN, which is expressed on the sinusoidal endothelial cells in the human liver and lymph nodes, also promotes HIV entry. These lectins preferentially bind to endogenous high-mannose oligosaccharides. DC-SIGN and L-SIGN were recently shown to enhance the infectivity of viruses pseudotyped with the Ebola GP. Another C-type lectin, the hepatic asialoglycoprotein receptor found exclusively in hepatocytes, recognizes GPs displaying N-linked sugar chains with terminal galactose residues and was initially identified as a receptor for Marburg virus. See also, Takada et al., Human Macrophage C-Type Lectin Specific for Galactose and N-Acetylglucosamine Promotes Filovirus Entry," *J. Virol.* 78(6):2943-2947 (2004).

A variety of C-type lectins have been cloned and may be prepared by rDNA or peptide synthesis. Representative sequences may be found in GenBank, e.g., CAC82936, C type lectin [*Mus musculus*]; CAC82936 C type lectin [*Mus musculus*]; AAB96837 C-type lectin [*Gallus gallus*]; CAA65480 C-Type lectin [*Homo sapiens*]; AAA02123 Sequence 2 from U.S. Pat. No. 4,882,422; AAA02451 Sequence 16 from U.S. Pat. No. 4,933,280; and AR022939, Sequence 6 from U.S. Pat. No. 5,792,648.

Perry et al., “Inhibition of Blood Clearance and Hepatic Tissue Binding of *Escherichia coli* by Liver Lectin-Specific Sugars and Glycoproteins,” *Inf. Imm*., January 1984, Vol. 43, p. 257-262, disclose that the mannose-N-acetylglucosamine hepatic lectin recognizes specific sugars on the surface of *E. coli* and may be centrally involved in the nonimmune clearance of nonfimbriated *E. coli* from the blood. At least three liver lectins specific for galactose-N-acetylgalactosamine (Gal-GalNac), mannose-N-acetylglucosamine (Man-GlcNac), and fucose (Fuc) residues have been isolated from mammalian livers. These have now been characterized and shown to be responsible for the blood clearance of glycoproteins.

It is further contemplated that the present nanostructures employ C-type lectins such as selectins. The adhesion of lymphocytes to endothelial cells is a necessary prelude to tissue inflammation. Intercellular adhesion molecule-I is a heavily glycosylated receptor molecule involved in mediating endothelial cell-lymphocyte binding. Selectins are molecules on endothelial cells, lymphocytes, or platelets that are involved in the first steps leading to adhesion with cells containing counter receptors with oligosaccharide conjugates (sialyl Lewis X is one such receptor molecule). In particular, sialyl Lewis X, NeuNAc23Galβ14(Fuc13)GlcNAcR, whose presence was noted in neutrophils, has been identified to be a ligand for selectins.

Selectins contain a carbohydrate-binding domain at their NH2 terminus and belong to the C-type lectin gene family of which activity is dependent on Ca2+. E- and P-selectin are expressed on activated vascular endothelial cells and the binding of these selectins to sialyl Lewis X on leukocytes allows them to roll, which leads to extravasation of leukocytes. L-selectin, on the other hand, is present on lymphocytes and binds to sulfated sialyl Lewis X oligosaccharides present in L-selectin receptors restricted to high endothelial venules.

Prevention of lymphocyte adhesion to endothelial cells in patients with diseases characterized by excessive inflammation has been the object of intense research. It has been demonstrated that it is the carbohydrate moiety of protein C (a plasma glycoprotein) that inhibits e-selectin mediated cell adhesion. Intravenous infusion of selectin-reactive oligosaccharides prevented selectin-dependent inflammatory lung injury.

All three selectins recognize sulfated and sialylated derivatives of the Lewis x [Lex: Gal14(Fuc13)GlcNAc] and Lewis a [Lea: Gal13(Fuc14)GlcNAc] trisaccharide cores with affinities in the millimolar range, and it is believed that variants of these structures are the carbohydrate determinants of selectin recognition.

As reported in Sanders et al., “L-Selectin-Carbohydrate Interactions: Relevant Modifications of the Lewis x Trisaccharide,” *Biochemistry,* 35 (47), 14862-14867, 1996, it has been shown that the mucin GlyCAM-1, a secreted physiological ligand for L-selectin, is capped with sulfated derivatives of sialyl Lewis x [sLex: Sia23Gal14(Fuc13)GlcNAc] and that sulfation is required for the high-affinity interaction between GlyCAM-1 and L-selectin. To elucidate the important sites of sulfation on Lex with respect to L-selectin recognition, the authors synthesized six sulfated Lex analogs and determined their abilities to block binding of a recombinant L-selectin-Ig chimera to immobilized GlyCAM-1. Our results suggest that 6-sulfo sLex binds to L-selectin with higher affinity than does sLex or 6'-sulfo sLex and that sulfation of sLex capping groups on GlyCAM-1 at the 6-position is important for L-selectin recognition.

Other lectins exist naturally on human cells. CD22 is a cell-surface receptor of resting mature B cells that recognizes sialic acid (Sia) in the natural structure Siaα2-6Galβ1-4GlcNAc (Powell, L. D., Jain, R. K., Matta, K. L., Sabesan, S., and Varki, A. (1995) J. Biol. Chem. 270, 7523-7532). See, Hanasaki et al., “Binding of Human Plasma Sialoglycoproteins by the B Cell-specific Lectin CD22,” *J. B. C., Mar.* 31, 1995, Vol. 270, No. 13, 7543-7550.

The presence of lectins on human cells may be used for targeting the present complexes. Robinson et al., “LEAPT: Lectin-directed enzyme-activated prodrug therapy,” PNAS 101(40): 14527-14532 (2004) report that synthetic glycopolymers and glycoproteins have been used as carriers of covalently conjugated drugs, bearing carbohydrate ligands that provide delivery specificity. Among these mechanisms, the interaction of carbohydrate-binding protein lectins with carbohydrates is one of potential utility that has been particularly highlighted by serum-clearance studies of glycoproteins by the asialoglycoprotein receptor (ASGPR) and the mannose receptor. The ASGPR protein is a membrane-bound, endocytic lectin found in abundance on the surface of hepatocytes in the liver. Gal is the carbohydrate ligand preferentially bound by the 50,000-500,000 copies of the ASGPR that are typically found on a liver cell hepatocyte surface.

Gems et al., “An abundantly expressed mucin-like protein from Toxocara canis infective larvae: The precursor of the larval surface coat glycoproteins,” *Proc. Natl. Acad. Sci. USA* Vol. 93, pp. 1665-1670, February 1996 describe a 730-bp cDNA from the gene encoding the apoprotein precursor of TES-120. The tandem repeat structure in the ST region of TES-120 and the heavy 0-glycosylation are typical of mucins. Vertebrate mucins fall into two categories: secreted mucins, such as MUC-2 and porcine submaxillary mucin, and cell-membrane-associated mucins, such as sialomucin (CD34), leukosialin (CD43), and MUC-1, previously described as episialin, pancreatic tumor, and mammary gland mucin, respectively Secreted mucins typically contain >500 amino acid residues, with a predominance of Thr over Ser. By these two criteria TES-120 more closely resembles a membrane mucin in being smaller in size (177 amino acid residues) and relatively rich in Ser, with a Ser/Thr ratio of 2.4.

TABLE 1

Lectins for targeting different cell types

| Lectin to be added | sugar specific to lectin to be used in glycosylated nanostructure | cell types binding lectin for biological complex |
|---|---|---|
| concanavalin A | α-mannose, α-glucose | lymphocytes |
| wheat germ agglutinin | N-acetylglucosamine | monocytes |
| peanut agglutinin | Galactose (1→3)-N-acetylgalactosamine | lymphoid, epithelial |
| *r communis* agglutinin | β-galactose | lymphocyte and transformed fibroblast |
| S-lectin | Galβ1-4Glc | variety, laminin |
| L-14 S-Lac human lectin | lactose --Gal(β1-4)glc | " |

Table 2 lists lectins, which are commercially available from Galab Technologies, Geesthacht Germany. These are used as ligands for affinity separation, and therefore have relatively high binding to the listed sugars.

TABLE 2

Lectins for targeting different saccharides in biological tissues

| Lectin Name | | Organism | Affinity |
|---|---|---|---|
| Mannose binding lectins | | | |
| Con A | Con-canavalin A | Canavalia ensiformis | branched α-mannosidic structures; high-mannose type, hybrid type and biantennary complex type N-Glycans |
| LCH | Lentil lectin | Lens culinaris | Fucosylated core region of bi- and triantennary complex type N-Glycans |
| GNA | Snowdrop lectin | Galanthus nivalis | α 1-3 and α 1-6 linked high mannose structures |
| Galactose/N-acetylgalactosamine binding lectins | | | |
| RCA | Ricinus communis Agglutinin, RCA$_{120}$ | Ricinus communis | Galβ1-4GlcNAcβ1-R |
| PNA | Peanut Agglutinin | Arachis hypogaea | Galβ1-3GalNAcα1-Ser/Thr (T-Antigen) |
| AIL | Jacalin | Artocarpus integrifolia | (Sia)Galβ1-3GalNAcα1-Ser/Thr (T-Antigen) |
| VVL | Hairy vetch lectin | Vicia villosa | GalNAcα-Ser/Thr (Tn-Antigen) |
| Sialic acid/N-acetylglucosamine binding lectins | | | |
| WGA | Wheat Germ agglutinin | Triticum vulgaris | GlcNAcβ1-4GlcNAcβ1-4GlcNAc, Neu5Ac (sialic acid) |
| SNA | Elderberry lectin | Sambucus nigra | Neu5Acα2-6Gal(NAc)-R |
| MAL | Maackia amurensis lectin | Maackia amurensis | Neu5Ac/ Gcα2-3Galβ1-4GlcNAcβ1-R |
| Fucose binding lectins | | | |
| UEA | Ulex europaeus agglutinin | Ulex europaeus | Fucα1-2Gal-R |
| AAL | Aleuria aurantia lectin | Aleuria aurantia | Fucα1-2Galβ1-4(Fucα1-3/4)Galβ1-4GlcNAc; R2-GlcNAcβ1-4(Fucα1-6)GlcNAc-R1 |

TABLE 3

| | | Other lectins |
|---|---|---|
| Agaricus bisporus | ABA | Fetuin; Galβ1-3GalNAc |
| Amaranthus caudatus | ACL | Galβ 1-3GalNAc, Neu5Acα2-3Galβ 1-3GalNAc; T-Antigen |
| Griffonia simplicifolia lectin I | GSL I | α-N-acetylgalactosamine, α-galactose |
| Griffonia simplicifolia lectin II | GSL II | terminal-α,β-GlcNAc; glycogen |
| Griffonia simplicifolia I B4 | GSL I B4 | α-D-galactosyl residues |
| Bauhinia purpurea alba | BPL | Galβ1-3GalNAc |
| Codium fragile | CFL | GalNAc |
| Datura stramonium | DSL | (GlcNAcβ1-4)$_3$GlcNAc = (Glcβ1-4)$_2$GlcNAc > Glcβ1-4GlcNAc >> GlcNAc |
| Dolichos biflorus | DBA | terminal FP > GalNAcα1-3GalNAc > GalNAcα1-3Gal; blood group A$_f$ (Forssman pentasaccharide: GalNAcα1-3GalNAcα1-3Galβ1-4Galβ1-4GlcNAc) |
| Erythrina coralldendron | ECor A | GalNAc/N-acetyllactosamin/ Lactose/D-Gal |
| Euonymos europaeus | EEA | Galα1-3(L-Fucα1-2)Galβ1,3/4-β-GlcNAc; Galα1-3Gal; blood group H structures |

TABLE 3-continued

| | | Other lectins |
|---|---|---|
| Glycine max | SBA | terminal α,βGalNAc > α,βGal |
| Helix aspersa | HAA | terminal αGalNAc residues |
| Helix pomatia | HPA | GalNAcα1-3GalNAc > α-GalNAc > α-GlcNAc >> α-Gal |
| Hippeastrum hybrid | HHL | (α1,3)/(α1,6) mannose; polymannose structures; yeast galactomannans |
| Lotus tetragonolobus | LTL | α-L-fucose |
| Lycopersicon esculentum | LEL | (GlcNAcβ 1-4)$_3$GlcNAc > (GlcNAcβ1-4)$_2$ GlcNAc > GlcNAcβ1-4GlcNAc |
| Maclura pomifera | MPA | terminal Galβ1-3GalNAc > GalNAcα 1-6Gal |
| Narcissus pseudonarcissus | NPA | terminal and internal α-D-mannosylresidues on glycoconjugates, preferably oligomannoses containing α1-6 linkages |
| Phaseolus coccineus | PCA | agglutination is not inhibited by monosaccharides but is inhibited by fetuin |
| Phaseolus vulgaris L | PHA-L | GlcNAcβ1,2Man, triantennary complex oligosaccharides |
| Phaseolus vulgaris E | PHA-E | Galβ1,4GlcNAcβ1,2Manα1,6 |
| Phytolacca americana | PWM | N-acetyl-β-D-glucosamine oligomers |
| Pisum sativum | PSA, PEA | branched α-man, complex type with N-acetylchitobiose-linked core α-fuc |
| Psophocarpus tetragonolobus I | PTL, WBA | α-galactosamine |
| Solanum tuberosum | STA | N-acetyl-β-D-glucosamine oligomers |
| Sophora japonica terminal | SJA | Galβ1,3GalNAc > Galβ 1,3GlcNAc > αβ,GalNAc > αβ,Gal |
| Wisteria floribunda | WFA, WFL | terminal N-acetylgalactosamine-α- or β-3 or 6-galactose |

Various Mucins, Mucin Mimics and Synthetic Polysaccharides

Exemplary mucins are oligomeric mucin glycoproteins MG1 and MG2, found in human saliva. MG2 is the product of the MUC7 gene. MG1 comprises predominantly MUC5B. See, Thomson, et al., "The salivary mucin MG1 (MUC5B) carries a repertoire of unique oligosaccharides that is large and diverse," Glycobiology, 2002, Vol. 12, No. 1 1-14. With regard to MG1 structures, the authors report that that (1) fucose was present in blood group H, Lea, Lex, Leb, and Ley epitopes; (2) NeuAc was mainly linked {alpha}2-3 to Gal or {alpha}2-6 to GalNAcol; and (3) the major internal structures were core 1 and core 2 sequences.

Salivary mucins contain a variety of oligosaccharide chains. Human oligomeric mucin (MG 1) contains 292 O-linked oligosaccharide chains per monomeric unit (that may form a "bottle brush"-like structure) and 118 oligosaccharide chains have sialic acids on non-reducing ends. Oligosaccharide chains of MG1 ranging from 1-20 residues are located mostly in clusters on the super-repeat subdomains of the central domain. The complex oligosaccharide chains of MG1 may be divided into three regions: the core, backbone and peripheral domains.

Human oligomeric mucin (MG1) contains 292 O-linked oligosaccharide chains per monomeric unit (that may form a "bottle brush"-like structure) and 118 oligosaccharide chains have sialic acids on non-reducing ends. Oligosaccharide chains of MG1 ranging from 1-20 residues are located mostly in clusters on the super-repeat subdomains of the central domain. The complex oligosaccharide chains of MG1 may be divided into three regions: the core, backbone and peripheral domains. See, Zalewsja et al., "Structure and biosynthesis of human salivary mucins," *Acta Biochimca Polonica*, Vol. 47 No. 4/2000 1067-1079.

With regard to binding to salivary mucins, it has been reported that GspB and Has, homologous surface glycoproteins of *Streptococcus gordonii*, bound low-molecular-weight salivary mucin MG2 and salivary agglutinin. See, Takamatsu et al., "Binding of the Streptococcal Surface Glycoproteins GspB and Hsa to Human Salivary Proteins," *Infection and Immunity*, March 2006, p. 1933-1940, Vol. 74, No. 3.

As referenced above, there is a wide variety of synthetic polysaccharide components that can be used with nanostructures to form the present complexes. Exemplified are repeating structures that are highly glycosylated like mucins. Bhavandan et al., "Purification and characterization of the MUC1 mucin-type glycoprotein, epitectin, from human urine: structures of the major oligosaccharide alditols," *Glycoconj J.* 1998 January; 15(1):37-49 report on the purification of the MUC1 glycoprotein, epitectin, a component of the human bladder epithelium, was purified from human urine. The neutral saccharides from both sources contain three common structures, namely Gal1-->3GalNAc, GlcNAc1-->6 (Gal1-->3) GalNAc and Gal1-->4GlcNAc-->6 (Gal1-->3) GalNAc. The sialic acid of urine epitectin consisted entirely of N-acetylneuraminic acid.

Other mucins include intestinal mucins, as described, e.g., in Robbie, et al., "Structural diversity and specific distribution of O-glycans in normal human mucins along the intestinal tract," *Biochem J.*, 2004 December 1; 384(Pt 2): 307-316. As reported there, purified human mucins from different parts of the intestinal tract (ileum, cecum, transverse and sigmoid colon and rectum) were isolated from two individuals with blood group ALeb (A-Lewisb). Oligosaccharides based on core 3 structures, GlcNAc(β1-3)GalNAc (where GlcNAc is N-acetyl-D-glucosamine and GalNAc is N-acetylgalactosamine), were widely distributed in human intestinal mucins. Core 5 structures, GalNAc(α1-3)GalNAc, were also recovered in all fractions. Highly fucosylated glycans, found specifically in the small intestine, were mainly based on core 4 structures, GlcNAc-(β1-3)[GlcNAc(β1-6)]GalNAc, whereas the sulpho-LeX determinant carrying core 2 glycans, Gal(β1-3)[GlcNAc(β1-6)]-GalNAc (where Gal is galactose), was recovered mainly in the distal colon. It was reported that part of this vast structural diversity could originate from bacterial degradation of mucins, since the intestinal microflora is believed to digest mucin oligosaccharides by secreting various linkage specific exoglycosidases.

Other lectin-binding glycans are proteoglycans, see U.S. Pat. No. 5,648,465 for a proteoglycan sequence.

General Description of Methods and Materials

GalNAc-Polymer-CNTs (Carbon Nanotubes)

FIG. 2a illustrates the structure of the present nanostructure complex in which a carbon nanotube is adsorbed to a plurality of molecules having a lipid portion and a glycopolymer portion. The presently exemplified polymers comprise a poly(methyl vinyl ketone) [poly(MVK)] backbone 204 decorated with —N-acetylgalactosamine (α-GalNAc) residues, 206, 208. (The α anomer refers to the —OH group orientation adjacent the —CH$_2$—OH.) These sugar residues are reminiscent of the O-linked glycans that decorate mucin glycoproteins. The C$_{18}$ lipid tail 202 provided a hydrophobic anchor for CNT 200 surface assembly. The coated CNTs formed stable aqueous solutions without obvious degradations for several months and were therefore poised for biological applications. We term CNTs coated with C$_{18}$-terminated, α-GalNAc-conjugated polymers "C$_{18}$-α-MM-CNTs", where "MM" denotes "mucin mimic."

FIG. 2A shows the structure of C$_{18}$-terminated, α-GalNAc-conjugated mucin mimic (C$_{18}$-α-MM) in both graphic and structural form. The mucin mimic polymers assemble on CNT surface in aqueous media through hydrophobic interaction between the C$_{18}$ lipid tails and CNT surface.

Complexation of Glyco-Nanostructures with Cells: Pathway I, Binding Lectin to Glyconanostrucutes, and Pathway II, Binding Lectin to Cells FIG. 2B shows a schematic diagram of two pathways for interfacing CNTs on cell surfaces to form a biological complex via carbohydrate-molecule binding. In pathway I, $C_{18}$-α-MM-coated CNTs were first bound to HPA, a hexavalent α-GalNAc binding lectin. The complex was then bound to cell surface glycoconjugates using available HPA binding sites presented on CNTs. In pathway II, HPA was first bound to cell surface glycoconjugates. The available HPA binding sites on cell surface were then bound to α-GalNAc residues on $C_8$-α-MM-coated CNTs.

In order to interface these functionalized CNTs with cells, we took advantage of the *Helix pomatia* agglutinin (HPA), a hexavalent lectin that is specific for α-GalNAc residues and is capable of crosslinking cells and glycoproteins[23]. HPA is a glycoprotein with about 7% carbohydrate content and, since this glycoprotein could be fractionated into at least 12 components by isoelectric focusing, the presence of different glycoforms is probable. The primary and tertiary structure of HPA is reported at Sanchez et al., "Biochemical and Structural Analysis of *Helix Pomatia* Agglutinin (HPA): A Hexameric Lectin with a Novel Fold," Biol. Chem., Vol. 281, Issue 29, 20171-20180, Jul. 21, 2006. The snail hemagglutinin consists of six identical polypeptide subunits, each containing one intra-chain disulfide bond and a carbohydrate binding site. In fact, two chains associate by a disulfide bridge, and the hexamer therefore consists of a non-covalent trimer of covalent dimers.

Experimental Procedures

The experiments below demonstrate that the complex of HPA with C18-α-MM-coated CNTs would possess sufficient available HPA binding sites for further complex formation with cell-surface glycoproteins (FIG. 2B—pathway I). Alternatively, HPA bound to cell surface glycans would present binding sites for α-GalNAc residues on C18-α-MM-coated CNTs (FIG. 1B-*pathway* II). In either scenario, binding of HPA to α-GalNAc residues would permit specific interaction of the cells and CNTs.

To evaluate pathway I (FIG. 2B), we required a means for detection of HPA binding to the C18-α-MM-coated CNTs. This was provided by the commercial reagent fluorescein isothiocyanate-conjugated HPA (HPA-FITC). We complexed C18-α-MM-coated CNTs with HPA-FITC, and the protein-modified CNTs were then incubated with Chinese hamster ovary (CHO) cells. The labeling observed by fluorescence microscopy (FIG. 3A) and flow cytometry analysis (FIG. 3B) suggested the formation of α-GalNAc-HPA complexes at both the CNT and cell surfaces. As a control, we performed the same experiment using CNTs coated with a similar polymer bearing α-linked GalNAc residues (C18-α-MM)22, which do not bind HPA. In this case, no fluorescent labeling of cells was observed (not shown).

In order to evaluate pathway II (FIG. 2B), we required a method for direct detection of C18-α-MM-coated CNTs that is independent of HPA. Thus, we synthesized a C18-α-MM polymer in which ~3% of the GalNAc residues were substituted with the fluorescent dye Texas Red (C18-α-MM/TR, FIG. 6). CHO cells were incubated with unmodified HPA to introduce α-GalNAc molecules onto the cell surface. The cells were then treated with various concentrations of C18-α-MM/TR-coated CNTs and analyzed by flow cytometry. As shown in FIG. 4A, dose-dependent labeling was observed (row I), and the labeling was dependent upon pre-complexation of the cells with HPA (row II). The control CNTs modified with C18-α-MM/TR showed no significant cell surface binding in the presence of HPA (FIG. 3A—row III). At the highest doses of C18-α-MM/TR-coated CNTs (>80 mg/mL), some non-specific fluorescent labeling of cells was observed. This may result from non-specific binding to the cell surface, or from internalization during the 1-hour incubation. However, at lower concentrations of C18-α-MM/TR-coated CNTs, cell labeling was highly specific.

The present invention facilitates the binding of a multiply glycosylated nanostructure to a cell having a corresponding glycosylation by an intermediary which is a lectin. Thus, the lectin serves, in effect, to cross-link a cell surface to a nanostructure. Viewed in this way, the nanostructure is provided with glycosylation that is the same glycosylation that is being targeted, so that a selected lectin can effectively bind to both the target cell and the glycosylated nanostructure.

EXAMPLES

Example 1

Synthesis of Labeled C18-α-MM-CNTs

The synthetic procedure for $C_{18}$-terminated, α-GalNAc-conjugated mucin mimics ($C_{18}$-α-MMs) and C18-terminated, β-GalNAc-conjugated mucin mimic (C18-β-MM) was described previously in the inventors' Angew. Chem. paper, referenced above. Synthetic procedures were as follows:
Synthesis of $C_{18}$ Functionalized Mucin Mimics with α-GalNAc Residues (C18-α-MMs).
Synthesis of $C_{18}$-Tailed Initiator (C18-ACPA):

To a solution of 4,4'-azobis(4-cyanopentanoic acid) (ACPA) (0.591 g, 2.11 mmol) in anhydrous $CH_2C_{12}$ (100 mL) in the dark at rt were added EDC (1.62 g, 8.44 mmol), DMAP (0.258 g, 2.11 mmol), $Et_3N$ (1.20 mL, 8.61 mmol), and octadecylamine (2.28 g, 8.44 mmol). The reaction mixture was stirred overnight at rt. The reaction mixture was diluted with $CH_2Cl_2$ and washed with saturated $NaHCO_3$ (aq.), water, and brine. The organic layer was dried over anhydrous $MgSO_4$. After evaporation of the solvent, the residue was separated by column chromatography (1:4 EtOAc/hexane) on silica gel to afford $C_{18}$-ACPA (0.76 g, 46%) as a white solid.
Synthesis of $C_{18}$-Poly(MVK)

Anhydrous p-dioxane (0.56 mL) was introduced into a 15-mL brown Schlenk tube containing methyl vinyl ketone (MVK) (0.56 mL, 6.73 mmol) and $C_{18}$-ACPA (50 mg, 64 μmol) under Ar. The reaction mixture was stirred for 72 h at 95° C. after degassing by four freezing and -thawing cycles. The reaction mixture was allowed to cool to rt, diluted with p dioxane (5 mL), and then added dropwise to excess diethyl ether (1 L) with vigorous stirring. The precipitate was filtered and washed with diethyl ether. The oligomers of low molecular weight were removed by dialysis in p-dioxane. The polymer was reprecipitated in excess diethyl ether (1 L), and the precipitate was dried in vacuo at 60° C. overnight. The polymer was soluble in dichloromethane, chloroform, acetonitrile, acetone, THF, and p-dioxane and insoluble in diethyl ether and hexane. The polymer is atactic as determined by $^1$H-NMR analysis.

Conjugation of α-Aminooxy GalNc to $C_{18}$-Poly(MVK) $C_{18}$-Poly (MVK)

To a solution of $C_{18}$-poly(MVK) (6.0 mg, 86 μmol based on carbonyl number) in THF (3 mL) were added α-aminooxy GalNAc (56.5 mg, 239 μmol) and aqueous acetic acid (0.1%, 1 mL). After 24 h at 95° C., the reaction mixture was allowed to cool to rt. All solvents were removed in vacuo, and then deionized water (2 mL) was introduced into the mixture to dissolve the partially ligated water-soluble polymer. After 48 h at 95° C., the reaction mixture was allowed to cool to rt, dialyzed in water to remove excess α-aminooxy GalNAc, neutralized by anion exchange and lyophilized to afford a fluffy white solid.
Synthesis of $C_{18}$ Functionalized Mucin Mimics with β-GalNAc Residues ($C_{18}$-β-MMs).

The synthesis of $C_{18}$-β-MMs was similar to C18-α-MMs. The only difference was that β-aminooxy GalNAc was used instead of α-aminooxy GalNAc in the final synthetic step.

In the present work, $C_8$-terminated, α-GalNAc-conjugated mucin mimic with Texas red (C18-α-MM/TR): To a solution of $C_{18}$-terminated poly(MVK)1 (6 mg, 85 μmol based on number repeating carbonyl units calculated from the MW as determined by GPC) in THF (5 mL) and $H_2O$ (2 mL) was added α-aminooxy GalNAc2 (40 mg, 171 μmol), texas red hydrazide (5 mg, 8 μmol) and acetic acid (5 μL). The solution was heated to 95° C., stirred for 24 h and concentrated in vacuo. The resulting solid was dissolved in $H_2O$ (7 mL) and refluxed for 48 h. The reaction mixture was cooled to ambient temperature, dialyzed in $H_2O$ and lyophilized to give the product (21 mg, 77% of carbonyls reacted) as a fluffy dark red solid. IR (KBr) 3434, 1658, 1641, 1381, 1005, 557, 463 cm-1; 1H NMR (400 MHz, $D_2O$, (see FIG. 5 for labeled compounds); GPC($H_2O$ eluent, polysaccharide standard), Mw=30.9×103 Da, PDI=3.18. $C_{18}$-terminated, β-GalNAc-conjugated mucin mimic with Texas red (C18-β-MM/TR): The synthesis of $C_{18}$-β-MM/TR was similar to $C_{18}$-α-MM/TR. The only difference was that β-aminooxy GalNAc2 was used instead of α-aminooxy GalNAc. Further details may be found in Chen, X.; Lee, G. S.; Zettl, A.; Bertozzi, C. R. Angew. Chem. Int. Ed. 2004, 43, 6111-6116, and Marcaurelle, L. A.; Shin, Y.; Goon, S.; Bertozzi, C. R. Org. Lett. 2001, 3, 3691.

Example 2

Preparation of Suspensions

High-purity single-walled carbon nanotubes (SWCNT) (HiPCO, >95%) were purchased from Carbon Nanotechnologies Inc., and high-purity multi-walled carbon nanotubes (MWNTs) (CVD, >95%) were purchased from Nanolab. In a typical preparation experiment, 1 mg of as-produced carbon nanotubes was suspended in 5 mL of aqueous C18-MM solution (0.1%~0.5%). The mixture was sonicated using a water-bath sonicator for 1 h. First, insoluble material was removed by low-speed centrifugation at 3,000×g for 30 min, and the product suspension was decanted from the insoluble material. Then the excess free glycopolymer was removed by dialysis of the suspension in a polycarbonate membrane against deionized water for 24 h. The resulting C18-MMNTs (C18-α-MM-SWNTs, C18-β-MM-SWNTs, C18-α-MM/TR-SWNTs, C18-β-MM/TR-SWNTs, C18-α-MMMWNTs, C18-β-MM-MWNTs, C18-α-MM/TR-MWNTs, C18-β-MM/TR-MWNTs) formed stable suspensions in aqueous solution. The concentrations of the resulting suspensions were calculated by evaporating the water and weighting the dried coated CNTs.

Example 3

Figure 2B:
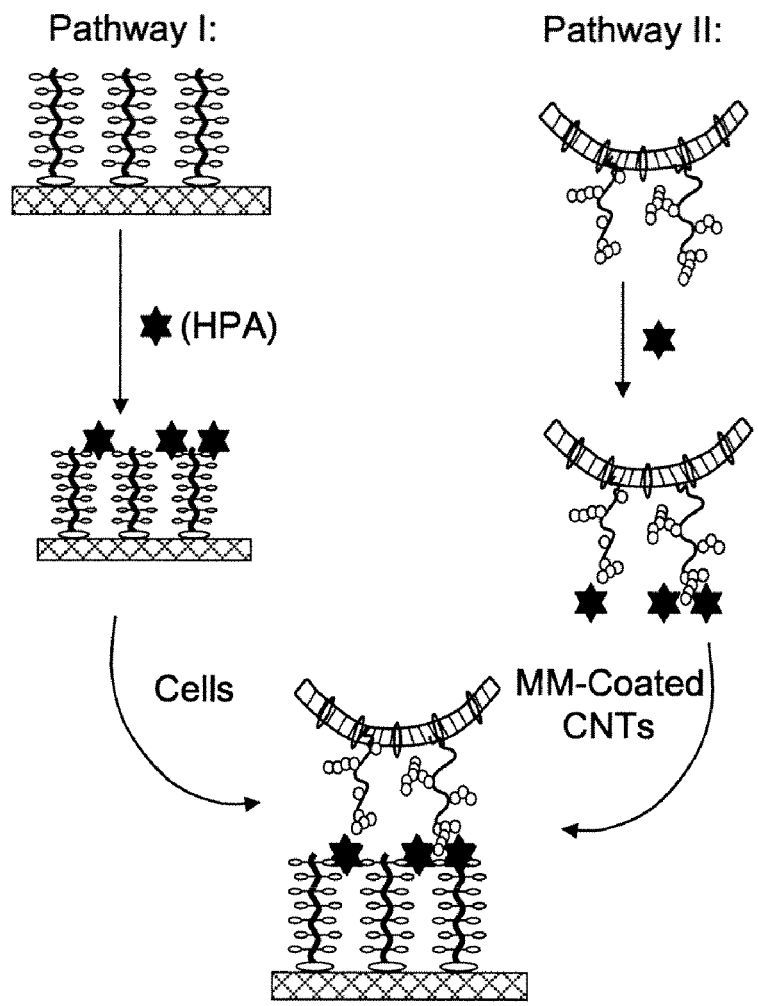
Figure 6:
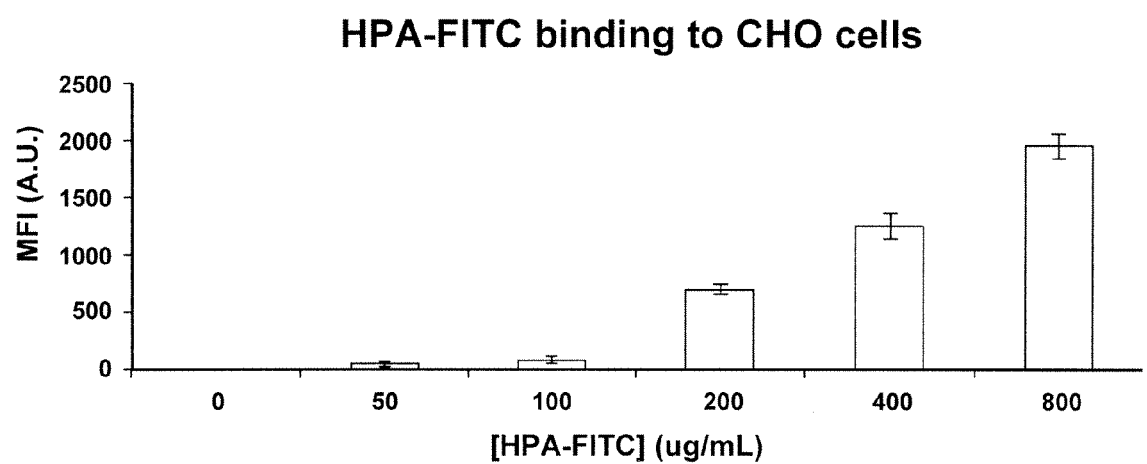
Figure 7C:
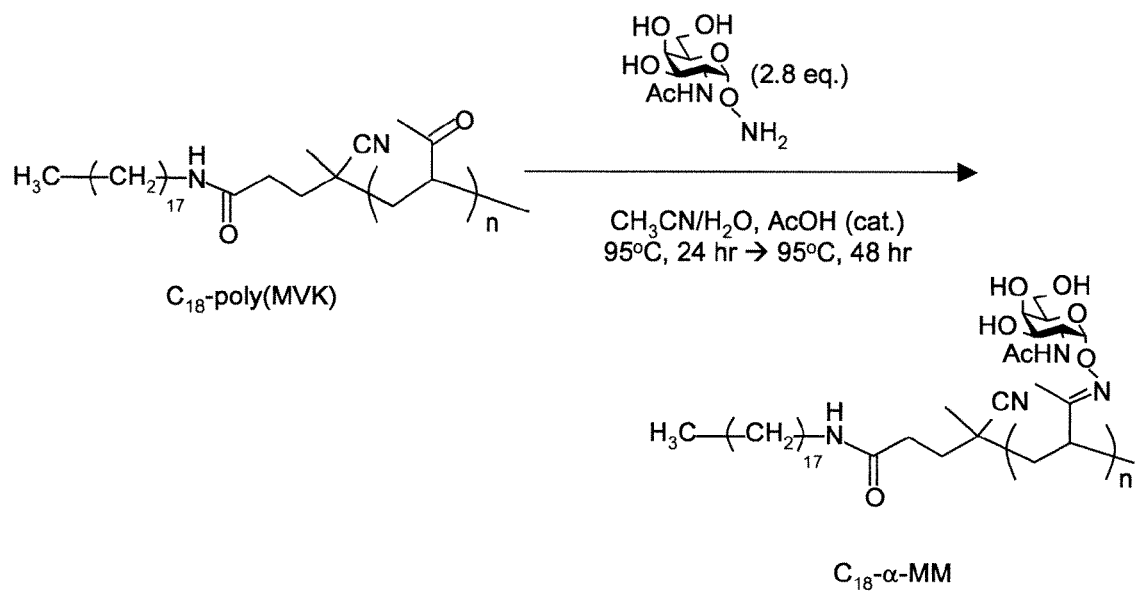

Preparation of Complex of HPA-FITC Bound C18-MM-CNTS (Pathway I in FIG. 2B):

In this example a lectin preparation is bound to a glycosylated nanostructure prior to contact with a tissue.

*Helix pomatia* agglutinin conjugated with fluorescein isothiocyanate (HPA-FITC) was obtained from EY-Laboratories. A 1-mL solution of HPA-FITC (100 μg/mL) in buffer (0.10 M Tris, and 0.15 M NaCl, pH 8.0) was added to the suspensions of mucin mimic-coated nanotubes (C18-α-MM-CNTs or C18-β-MM-CNTs) in H2O (1 mL). An additional 0.5 mL of buffer was added and the reactions were incubated for 1 h at rt in the dark. After incubation, the solutions were all subjected to dialysis against the buffer for 48 h. The dialyzed solutions were analyzed at 510-550 nm using a fluorescence microplate reader (excitation wavelength 492 nm). The concentrations were calculated as described above. The characterized solutions were then used for cell surface binding experiments.

Example 4

Microscopic and Flow Cytometry Analysis Showing Binding to Cells with Lectin Cross Linking Cell culture conditions: All cell lines were maintained in a 5% CO2, water-saturated atmosphere at 37° C. and media were supplemented with penicillin (100 unit/mL), streptomycin (0.1 mg/mL) and 10% FCS unless otherwise indicated. CHO cells were grown in Ham F12 nutrient mixture. Jurkat cells were grown in RPMI-1640 media.

Pathway I: $C_{18}$-α-MM-Coated CNTs were First Bound to HPA, a Hexavalent α-GalNAc Binding Lectin. The Complex was then Bound to Cell Surface Glycoconjugates Using Available HPA Binding Sites Presented on CNTS Cell surface binding of HPA-FITC-conjugated C18-MM-CNTs (Pathway I in FIG. 1B): Fluorescence Microscopy—CHO Cells were seeded onto glass slides mounted with tissue culture wells (LABTEK) and allowed to adhere for 2 d. The cells were washed 3 times with PBS, and then fixed in 3% paraformaldehyde in PBS. After three washes, cells were blocked in PBS with 1% bovine serum albumin for 20 min, followed by the addition of C18-MM-CNT-HPA-FITC complex. After a 1-h incubation at rt in the dark, the cells were washed 3 times. The cells were then mounted using Vectashield with 4,6-diamidino-2-phenylindole (Vector Laboratories). A Zeiss Axiovert 200M inverted microscope equipped with a 63×1.4 NA Plan-Apochromat oil immersion lens was employed for imaging. A 175W xenon lamp housed in a Sutter DG4 illuminator linked to the microscope by an optical fiber assured shuttering and illumination. Images were acquired using a CoolSNAP HQ CCD camera (Roper Scientific). Slidebook software (Intelligent Imaging Solutions) was used to control the microscope and the camera.

Flow Cytometry—Cells ($2\times10^6$) were seeded in a 10-cm dish for 3 d. The cells were lifted with 1 mM EDTA in PBS, washed, and counted. Flow cytometry analysis was performed on 500,000 cells. The cells were pelleted (3,500 rmp, 3 min) and washed twice with 200 μL of PBS containing 1% FCS. Cells were then treated with HPA-FITC-conjugated C18-MM-CNTs for 1 h at rt in the dark. After incubation, cells were pelleted, washed three times and analyzed using a FACScalibur flow cytometer (BD Biosciences).

Example 5

Titration of Binding of HPA to Cell Surfaces: Pathway II

This example relates to Pathway II, where a lectin (HPA) is bound to a tissue (cell surface glycans) prior to contact with the glycosylated nanostructure. The HPA on the cell surface present binding sites for α-GalNAc residues on $C_{18}$-α-MM-coated CNTs.

In order to determine the appropriate condition for complexation of HPA and cells (FIG. 2B—pathway II), cells were incubated with various dilutions of HPA-FITC and then analyzed by flow cytometry. The cells were pelleted and washed twice with 200 μL of PBS containing 1% FCS.

Cells were then treated with various concentrations of HPA-FITC for 1 h at rt in the dark. After incubation, the cells were pelleted, washed three times and analyzed using a FACScalibur flow cytometer (BD Biosciences). The cells were pelleted, washed three times and analyzed using a FACScalibur flow cytometer (BD Biosciences). The results are shown in FIG. 6.

Based on those results, a concentration of HPC-FITC (400 μg/mL) that produced robust cell surface labeling at sub-saturating levels was chosen. The assumption was made that free HPA binding sites are still available at this concentration, permitting addition binding to glycopolymer-coated CNTs. Binding of HPA-coated cells to $C_{18}$-MM/TR-CNT (Pathway I in FIG. 2B): Cells (0.5×106) were pelleted (3,500 rmp, 3 min) and washed twice with 200 μL of PBS containing 1% FCS. Cells were then treated with unmodified HPA (400 μg/mL) for 1 h at rt, followed by washing with buffer for 3 times. The cells were then incubated with $C_{18}$-MM/TR-CNTs for 1 h at rt in the dark. After incubation, cells were pelleted, washed three times and analyzed by flow cytometry.

Example 6

Cytotoxicity Assays

Recent reports that unfunctionalized CNTs show potent cytotoxicity towards alveolar macrophages[16], HacaT cells[17], and HEK293 cells[18] have stimulated concern regarding their potential utility in biological systems. We were therefore interested in evaluating the cytotoxicity of our glycopolymer-coated CNTs. CHO cells were cultured with $C_{18}$-α-MM-, $C_{18}$-α-MM/TR-, $C_{18}$-α-MM/TR-, or HPA-FITC-conjugated, $C_{18}$-α-MM-coated CNTs (each at 100 μg/mL) for 3 days. In control experiments, the cells were cultured with unmodified CNTs or with media alone. Viable cells were counted each day (FIG. 3*b*). Cells cultured with the glycopolymer-coated CNTs were indistinguishable from cells grown in the absence of CNTs. By contrast, cells cultured with unmodified CNTs were unable to expand during the course of the experiment. Presumably, the unmodified CNTs either inhibited cell growth or induced cell death at a rate comparable to the proliferation rate. Similar results were obtained with Jurkat cells (not shown). Thus, the glycopolymer coating renders the CNTs nontoxic while simultaneously providing a means for specific cell surface binding[24].

CHO cells—Cells were seeded at a density of 1.25×105 cells/mL and incubated with C18-α-MM-, C18-α-MM/TR-, C18-β-MM/TR-, or HPA-FITC-conjugated, C18-α-MM-coated CNTs (each at 100 μg/mL) for 3 d. In control experiments, the cells were cultured with unmodified CNTs or with media alone. Cells were washed twice with PBS and then trypsinized with 0.25% trypsin-EDTA (PBS, pH 7.4), resuspended in media and counted every 24 h.

Jurkat cells—Cells were seeded at a density of 1.25×105 cells/mL and incubated with C18-α-MM-, C18-α-MM/TR-, C18-β-MM/TR-, or HPA-FITC-conjugated, C18-α-MM-coated CNTs (each at 100 μg/mL) for 3 d. In control experiments, the cells were cultured with unmodified CNTs or with media alone. Cells were counted every 24 h.

CONCLUSION

The above specific description is meant to exemplify and illustrate the invention and should not be seen as limiting the scope of the invention, which is defined by the literal and equivalent scope of the appended claims. Any patents or publications mentioned in this specification are indicative of levels of those skilled in the art to which the patent pertains and are intended to convey details of the invention which may not be explicitly set out but which would be understood by workers in the field. Such patents or publications are hereby incorporated by reference to the same extent as if each was specifically and individually incorporated by reference, as needed for the purpose of describing and enabling the method or material referred to.

REFERENCES

1. Michalet, X.; Pinaud, F. F.; Bentolila, L. A.; Tsay, J. M.; Doose, S.; Li, J. J.; Sundaresan, G.; Wu, A. M.; Gambhir, S. S.; Weiss, S., *Science,* 2005, 307, 538-544.
2. Kasili, P. M.; Song, J. M.; Vo-Dinh, T., *J. Am. Chem. Soc.,* 2004, 126, 2799-2806.
3. Wu, W. Z.; Huang, W. H.; Wang, W.; Wang, Z. L.; Cheng, J. K.; Xu, T.; Zhang, R. Y.; Chen, Y.; Liu, J., *J. Am. Chem. Soc.,* 2005, 127, 8914-8915.
4. Mattson, M. P.; Haddon, R. C.; Rao, A. M., *J. Mol. Neurosci.,* 2000, 14, 175-182.
5. Andersson, H.; van den Berg, A., *Curr. Opin. Biotech.,* 2004, 15, 44-49.
6. Lin, Y.; Taylor, S.; Li, H. P.; Fernando, K. A. S.; Qu, L. W.; Wang, W.; Gu, L. R.; Zhou, B.; Sun, Y. P., *J. Mater. Chem.,* 2004, 14, 527-541.
7. Chen, R. J.; Bangsaruntip, S.; Drouvalakis, K. A.; Kam, N. W. S.; Shim, M.; Li, Y. M.; Kim, W.; Utz, P. J.; Dai, H. J., *Proc. Natl. Acad. Sci. U.S.A.,* 2003, 100, 4984-4989.
8. Wang, J.; Musameh, M.; Lin, Y. H., *J. Am. Chem. Soc.,* 2003, 125, 2408-2409.
9. O'Connell, M. J.; Bachilo, S. M.; Huffman, C. B.; Moore, V. C.; Strano, M. S.; Haroz, E. H.; Rialon, K. L.; Boul, P. J.; Noon, W. H.; Kittrell, C.; Ma, J. P.; Hauge, R. H.; Weisman, R. B.; Smalley, R. E., *Science,* 2002, 297, 593-596.
10. Cherukuri, P.; Bachilo, S. M.; Litovsky, S. H.; Weisman, R. B., *J. Am. Chem. Soc.,* 2004, 126, 15638-15639.
11. Barone, P. W.; Baik, S.; Heller, D. A.; Strano, M. S., *Nat. Mater.,* 2005, 4, 86-U16.
12. Kam, N. W. S.; O'Connell, M.; Wisdom, J. A.; Dai, H. J., *Proc. Natl. Acad. Sci. U.S.A.,* 2005, 102, 11600-11605.
13. Kam, N. W. S.; Jessop, T. C.; Wender, P. A.; Dai, H. J., *J. Am. Chem. Soc.,* 2004, 126, 6850-6851.
14. Pantarotto, D.; Singh, R.; McCarthy, D.; Erhardt, M.; Briand, J. P.; Prato, M.; Kostarelos, K.; Bianco, A., *Angew. Chem. Int. Ed.,* 2004, 43, 5242-5246.
15. Kam, N. W. S.; Dai, H. J., *J. Am. Chem. Soc.,* 2005, 127, 6021-6026.
16. Jia, G.; Wang, H. F.; Yan, L.; Wang, X.; Pei, R. J.; Yan, T.; Zhao, Y. L.; Guo, X. B., *Environ. Sci. Technol.,* 2005, 39, 1378-1383.
17. Shvedova, A. A.; Castranova, V.; Kisin, E. R.; Schwegler-Berry, D.; Murray, A. R.; Gandelsman, V. Z.; Maynard, A.; Baron, P., *J. Toxicol. Environ. Health, Part A* 2003, 66, 1909-1926.
18. Cui, D. X.; Tian, F. R.; Ozkan, C. S.; Wang, M.; Gao, H. J., *Toxicol. Lett.,* 2005, 155, 73-85.
19. Collins, B. E.; Paulson, J. C., *Curr. Opin. Chem. Biol.,* 2004, 8, 617-625.
20. Hollingsworth, M. A.; Swanson, B. J. *Nat. Rev. Cancer,* 2004, 4, 45-60.
21. Helenius, A.; Aebi, M., *Science,* 2001, 291, 2364-2369.
22. Chen, X.; Lee, G. S.; Zettl, A.; Bertozzi, C. R., *Angew. Chem. Int. Ed.,* 2004, 43, 6111-6116.
23. Lisgarten, J. N.; Chattopadhyay, T. K.; Pitts, J. E.; Palmer, R. A.; Reynolds, C. D.; Dao-Thi, M. H.; Van Driessche, E.; Beeckmans, S., *Acta. Crystallogr. D Biol. Crystallogr.,* 1999, 55, 1903-1905.
24. Sayes and Ausman et al., recently reported that CNTs functionalized with phenyl sulfonic acid or phenyl carboxylic acid show reduced cytotoxicity. C. M. Sayes et al., *Toxicol. Lett.* 2006, 161, 135-142.

What is claimed is:

1. A biological complex comprising:
   (a) a biological tissue having at least one cell, said cell having thereon a glycosylated cell surface molecule; and
   (b) a glycosylated nanostructure, comprising a carbon nanotube bound to a carbohydrate; and
   (c) an exogenous polyvalent lectin bound to said glycosylated nanostructure and (ii) to said glycosylated cell surface molecule,
   whereby said glycosylated nanostructure complexes to said tissue based on lectin glycosylation recognition.
2. The complex of claim 1 where the tissue comprises a living mammalian cell.
3. The complex of claim 2 where the living cell is a breast cancer cell, an epithelial cell or a blood cell.
4. The complex of claim 1 where the glycosylated nanostructure comprises a sugar that is at least one of GalNac, Gal1, Fuc, and GLcNAc1.
5. The complex of claim 1 where the glycosylated nanostructure comprises a mucin mimic comprising an aliphatic portion and a portion having repeated sugar bearing units.
6. The nanostructure of claim 1 wherein the glycosylated nanostructure comprises a synthetic polysaccharide.
7. The nanostructure of claim 6 wherein the synthetic polysaccharide comprises a lipid portion adsorbed thereto and selected from the group consisting of: linear polyethylene, polypropylene, polyvinylpyrrolidone (PVP), polystyrene sulfonate (PSS), poly{(m-phenylenevinylene)-co-[(2,5-dioctyloxy-p-phenylene)vinylene]} (PmPV), poly{(2,6-pyridinylenevinylene)-co-[(2,5-dioctyloxy-p-phenylene)vinylene]}(PPyPV), poly{(5-alkoxy-m-phenylenevinylene)-co-[(2,5-dioctyloxy-p-phenylene)vinylene]} (PAmPV), and polystyrene.
8. The complex of claim 1 where the glycosylated surface molecule is N-acetyl galactosamine (GalNac).
9. The complex of claim 1 where the glycosylated nanostructure further comprises a label.
10. The complex of claim 9 where said label is fluorescent.
11. The complex of claim 1 wherein the polyvalent lectin is a C-type lectin.

12. The complex of claim 1 where the lectin is bound to said surface lectin present on a cell, and is cluster of differentiation-22 (CD22) or asialoglycoprotein receptor (AS-GPR).

13. A method of forming a complex as recited in claim 1 comprising a nanostructure on a living cell surface, comprising the steps of:
 (a) preparing a complex comprising a nanostructure and a lipid-polysaccharide, thereby forming said glycosylated nanostructure;
 (b) formulating said complex for administration to an organism; and
 (c) administering the complex and a polyvalent lectin to an organism, whereby the polysaccharide binds specifically to said polyvalent lectin on a cell surface.

14. The method of claim 13 where the lectin is administered separately from the complex.

15. The method of claim 13 where the lectin is bound to the complex prior to administration, said lectin cross linking between the complex and the cell surface.

16. The method of claim 13 where the lectin binds specifically to GalNac.

17. A method for labeling cells, by forming a complex as defined in claim 1, comprising the steps of:
 (a) preparing a composition comprising said glycosylated nanostructure, comprising a labeled lipid-polysaccharide; and
 (b) contacting the cells with the composition, whereby the polysaccharide binds specifically to a lectin on a cell surface, forms a complex as recited in claim 1, and labels the cells.

18. The method of claim 17 where the cells are in culture.

19. The method of claim 17 further comprising the step of binding a lectin to the complex prior to contacting the cells with the complex.

* * * * *

UNITED STATES PATENT AND TRADEMARK OFFICE
CERTIFICATE OF CORRECTION

PATENT NO. : 8,257,932 B2
APPLICATION NO. : 12/034388
DATED : September 4, 2012
INVENTOR(S) : Xing Chen et al.

It is certified that error appears in the above-identified patent and that said Letters Patent is hereby corrected as shown below:

IN THE CLAIMS

Column 26, line 35 (claim 1), delete "(ii)".

Signed and Sealed this
Tenth Day of March, 2015

Michelle K. Lee
*Deputy Director of the United States Patent and Trademark Office*